(12) United States Patent
Matousek et al.

(10) Patent No.: US 12,291,550 B2
(45) Date of Patent: May 6, 2025

(54) METHOD FOR FUNCTIONALIZATION OF AN AROMATIC AMINO ACID OR A NUCLEOBASE

(71) Applicants: CF PLUS CHEMICALS S.R.O., Brno (CZ); USTAV ORGANICKE CHEMIE A BIOCHEMIE AV CR, V.V.I., Prague (CZ); MIKROBIOLOGICKY USTAV AV CR, V.V.I., Prague (CZ)

(72) Inventors: Vaclav Matousek, Zliv (CZ); Petr Beier, Prague (CZ); Petr Novak, Dolni Brezany (CZ)

(73) Assignees: CF PLUS CHEMICALS S.R.O., Brno (CZ); USTAV ORGANICKE CHEMIE A BIOCHEMIE AV CR, V.V.I., Prague (CZ); MIKROBIOLOGICKY USTAV AV CR, V.V.I., Prague (CZ)

( * ) Notice: Subject to any disclaimer, the term of this patent is extended or adjusted under 35 U.S.C. 154(b) by 590 days.

(21) Appl. No.: 17/603,400

(22) PCT Filed: May 5, 2020

(86) PCT No.: PCT/CZ2020/050029
§ 371 (c)(1),
(2) Date: Oct. 13, 2021

(87) PCT Pub. No.: WO2020/224686
PCT Pub. Date: Nov. 12, 2020

(65) Prior Publication Data
US 2022/0177514 A1 Jun. 9, 2022

(30) Foreign Application Priority Data

May 6, 2019 (EP) ..................................... 19172756

(51) Int. Cl.
| | | |
|---|---|---|
| C07K 1/107 | (2006.01) |
| C07B 39/00 | (2006.01) |
| C07C 43/225 | (2006.01) |
| C07C 69/02 | (2006.01) |
| C07C 217/60 | (2006.01) |
| C07C 227/16 | (2006.01) |
| C07C 247/04 | (2006.01) |
| C07C 309/58 | (2006.01) |
| C07D 209/16 | (2006.01) |
| C07D 233/64 | (2006.01) |
| C07H 1/00 | (2006.01) |

(52) U.S. Cl.
CPC ............ C07K 1/1077 (2013.01); C07B 39/00 (2013.01); C07C 43/225 (2013.01); C07C 69/02 (2013.01); C07C 217/60 (2013.01); C07C 227/16 (2013.01); C07C 247/04 (2013.01); C07C 309/58 (2013.01); C07D 209/16 (2013.01); C07D 233/64 (2013.01); C07H 1/00 (2013.01)

(58) Field of Classification Search
None
See application file for complete search history.

(56) References Cited

U.S. PATENT DOCUMENTS

2019/0040036 A1 2/2019 Matousek et al.

FOREIGN PATENT DOCUMENTS

WO 2016019475 A1 2/2016

OTHER PUBLICATIONS

Yagupolskii, L. M. et al. "A New Method of Perfluoroalkylation" Synthesis 1978; 1978(11): 835-837 (Year: 1978).*
Shimizu, R. et al. "Direct C2-trifluoromethylation of indole derivatives catalyzed by copper acetate" Tetrahedron Letters 51 (2010) 5947-5949 (Year: 2010).*
Hojczyk, K. N. et al. "Trifluoromethoxylation of Arenes: Synthesis of ortho-Trifluoromethoxylated Aniline Derivatives by OCF3 Migration" Angew. Chem. Int. Ed. 2014, 53, 14559-14563 (Year: 2014).*
Matousek, V. et al. "Expanding the Scope of Hypervalent Iodine Reagents for Perfluoroalkylation: From Trifluoromethyl to Functionalized Perfluoroethyl" Chem. Eur. J. 2016, 22, 417-424 (Year: 2016).*
Jiang, H. et al. "Designing new Togni reagents by computation" Chem. Commun., 2019, 55, 5667; Published online Apr. 29, 2019 (Year: 2019).*
Niedermann, K. et al. "New hypervalent iodine reagents for electrophilic trifluoromethylation and their precursors: synthesis, structure, and reactivity" Tetrahedron 66 (2010) 5753-5761 (Year: 2010).*
Liebing, P. et al. "Supramolecular Aggregation of Perfluoroorganyl Iodane Reagents in the Solid State and in Solution" Eur. J. Org. Chem. 2018, 3771-3781 (Year: 2018).*
Matousek V; Vaclavik J; Hajek P; Charpentier J; Blastik Z E; Pietrasiak E; Budinska A; Togni A; Beier P; "Expanding the Scope of Hypervalent Iodine Reagents for Perfluoroalkylation: From Trifluoromethyl to Functionalized Perfluoroethyl"; Chemistry a European Journal, vol. 22, 2016, pp. 417-424, retrieved Oct. 12, 2021, Abstract only.
International Search Report and Written Opinion for corresponding PCT application No. PCT/CZ2020/050029, mailed Oct. 28, 2020.

* cited by examiner

*Primary Examiner* — Medhanit W Bahta
(74) *Attorney, Agent, or Firm* — Notaro, Michalos & Zaccaria P.C.

(57) ABSTRACT

A method for functionalization of an aromatic amino acid or a nucleobase with a fluoroalkyl-containing moiety RF, wherein the aromatic amino acid is reacted in the presence of at least one reductant with at least one hypervalent iodine fluoroalkyl reagent carrying the fluoroalkyl-containing moiety RF is disclosed. Novel hypervalent iodine fluoroalkyl reagents is also disclosed.

11 Claims, 7 Drawing Sheets

Specification includes a Sequence Listing.

METHOD FOR FUNCTIONALIZATION OF AN AROMATIC AMINO ACID OR A NUCLEOBASE

FIELD OF THE INVENTION

The invention relates to reductant-triggered functionalisation of aromatic amino acids or nucleobases with fluoroalkyl groups based on reaction of hypervalent iodine fluoroalkyl reagents with the aromatic amino acid or nucleobase (which may be incorporated in a protein or a nucleic acid) in the presence of a reductant.

BACKGROUND ART

Methods for direct late-stage functionalisation of organic compounds and especially biomolecules are highly sought after. Of special interest are methods that allow fast and selective protein functionalisation, ideally targeting one specific amino acid. Typical standard methods include lysine functionalisation with N-hydroxysuccinimide esters of carboxylic acids, or alkylation of free cysteines with iodoacetamides or maleimides. In comparison, methods that enable direct functionalisation of aromatic amino acids are less common. Examples include ene-type functionalisation of tyrosine residues with triazolodiones or azo coupling using diazonium based reagents, such as 4-formylbenzenediazonium hexafluorophosphate.

Tryptophan residues were selectively modified using metallocarbenes in aqueous media. A carbene derived from a vinyl diazo compound and rhodium catalyst reacted with both nitrogen and C(2) atom of tryptophan indole ring. The authors have carried out modification of horse heart myoglobin and the activity was preserved after the conjugation. The bioconjugation reaction was performed in ethylene glycol as a biocompatible cosolvent and using hydroxylamine hydrochloride to enhance the activity of catalyst. A transition metal-free procedure based on stabilized aminoxyl radicals for tryptophan-selective bioconjugation was reported by Seki et al. (Seki, Y.; Ishiyama, T.; Sasaki, D., et al., *Journal of the American Chemical Society* 2016, 138 (34), 10798-10801). However, methods for direct functionalisation of histidine are more scarce and this is even more so for phenylalanine residues for which there are no biocompatible and rapid bioconjugation methods.

Hypervalent cyclic $CF_3$-iodine reagents are known as Togni reagents (Eisenberger P., Gischig, S., Togni A., Chem. Eur. J. 2006, 12, 2579-2586). Fluoroalkylation reagents of the Togni type suitable for fluoroalkylation of a broad variety of compounds with a broad range of fluoroalkyl-containing moieties were introduced in WO 2016/019475. WO 2016/019475 describes the synthesis of the Togni-type fluoroalkylation reagents, and briefly mentions their usability for fluoroalkylating certain types of reactive nucleophiles (page 8). These fluoroalkylation reactions are carried out by contacting the substrate (nucleophile) with the Togni-type reagent. When the substrate contains an indole ring, the reaction is slow (overnight), has a rather low yield, and a catalysis by a copper compound is needed, i.e., it does not comply with the requirement for transition metal-free procedures.

The aim of the present invention is to provide a transition metal-free method for direct late-stage functionalisation of aromatic amino acids or nucleobases and especially biomolecules containing these amino acids or nucleobases, which would be extremely fast, versatile and generally applicable. In particular, the method should be suitable for functionalization of four standard aromatic amino acids (phenylalanine, tryptophan, tyrosine, histidine) and of the nucleobases.

DISCLOSURE OF THE INVENTION

The object of the invention is a method for functionalization of an aromatic amino acid or a nucleobase with a fluoroalkyl-containing moiety $R_F$, wherein the aromatic amino acid is reacted in the presence of at least one reductant with at least one hypervalent iodine fluoroalkyl reagent (Togni-type reagent).

The Togni-type reagents used in the present invention have a general formula 1

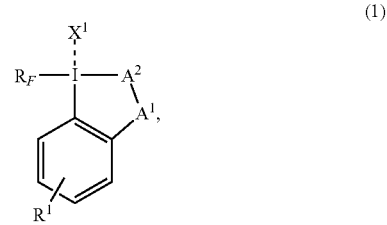

(1)

wherein
$R^1$ is selected from H, C1-C4 alkyl, $Me(OCH_2CH_2)_nO$, wherein n=1-10,
$X^1$ is not present or is selected from chloride, tetrafluoroborate, hexafluorophosphate, trifluoromethanesulfonate, methanesulfonate, toluenesulfonate, fluoride, bromide, $(F(CF_2)_sSO_2)_2N^+$, wherein s=1 to 4, C1-C6 carboxylate, fluorinated C1-C6 carboxylate, hexafluoroantimonate;
$A^1$ is not present or is selected from
carbonyl group (C=O),
$R^2$—C—$R^3$, where $R^2$ and $R^3$ are independently selected from fluorine, chlorine, hydrogen, $CF_3$, $C_1$-$C_4$ alkyl, phenyl, phenyl substituted by fluorine, chlorine and/or $C_1$-$C_4$ alkyl, omega-methoxy-($C_1$-$C_4$)alkyl, or $R^2$ and $R^3$ together with the carbon atom to which they are bound form 1,1-cyclobutylene, 1,1-cyclopentylene, 1,1-cyclohexylene, 1,1-(4-oxacyclohexylene);
$A^2$ is not present or is selected from
hydroxyl group (OH),
oxygen (—O—),
$C_{1-4}$ alkoxy,
$OSiR^4R^5R^6$, wherein $R^4,R^5,R^6$ are independently selected from methyl, ethyl, n-propyl, propyl and phenyl;
$R^7N$, wherein $R^7$ is selected from $C_{1-10}$ alkyl, phenyl-substituted $C_{1-10}$ alkyl, 4-chlorophenyl-substituted $C_{1-10}$ alkyl, and $CH_3(OCH_2CH_2)_n$;
$R^8CO$—, wherein $R^8$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_mCOOQ$, —$(CX_2)_mSO_3Q$, wherein m=2-3, -phenyl-$SO_3Q$, -phenyl-COOQ, —$(CX_2)_m COO$—, —$(CX_2)_mSO_3$—, wherein m=2-3, -phenyl-$SO_3$—, -phenyl-COO—,
$X_2$=F or Cl, $X_3$=H, $CH_3$, F or Cl,
Q is selected from lithium, sodium, potassium, rubidium, cesium, tetra (C1-C4 alkyl, phenyl, benzyl) ammonium (such as tetramethylammonium, tetraethylammonium, tetrapropylammonium, tetrabutylammonium, benzyltriethylammonium, phenyltrimethylammonium), tri (C1-C4 alkyl, phenyl, benzyl)pyridinium;

$R^9C(O)O-$, wherein $R^9$ is selected from $C_{1-10}$ alkyl, phenyl-substituted $C_{1-10}$ alkyl, $CH_3(OCH_2CH_2)_o-$, wherein o=1-10, $Cl^-Me_3N^+(CH_2)_p-$, wherein p=1-10, $-(CX_2)_mCOOQ$, $-(CX_2)_m SO_3Q$, wherein m=2-3, -phenyl-$SO_3Q$, -phenyl-COOQ, $-(CX_2)_m COO-$, $-(CX_2)_m SO_3-$, wherein m=2-3, -phenyl-$SO_3-$, -phenyl-COO—, $X_2$=F or Cl, $X_3$=H, $CH_3$, F or Cl, Q is selected from lithium, sodium, potassium, rubidium, cesium, tetra (C1-C4 alkyl, phenyl, benzyl) ammonium (such as tetramethylammonium, tetraethylammonium, tetrapropylammonium, tetrabutylammonium, benzyltriethylammonium, phenyltrimethylammonium), tri (C1-C4 alkyl, phenyl, benzyl)pyridinium;

$R_F$ is $-CF_2-A^3-A^4$, wherein $A^3$ is not present and $A^4$ is fluorine, or phenylsulfanyl (PhS) group, or $A^3$ is $CF_2$ and $A^4$ is fluorine, $C_{1-10}$ perfluoroalkyl, phenoxy, $C_{1-10}$ alkoxy, phenylsulfanyl, N-imidazolyl, N-pyrazolyl, N-benzimidazolyl, N-triazoyl, N-(2-methyl)imidazolyl, $CH_3(OCH_2CH_2)_nO$, where n=1-10, $Cl^-MeH_2N^+(CH_2)_m$ wherein r=1-10, $Cl^-MeH_2N^+(CH_2)_2$-phenyloxy, $C_{1-10}$ alkyl, ethenyl, ethynyl, omega-azido $C_{1-10}$ alkyl, omega-amino $C_{1-10}$ alkyl, omega-ethynyl $C_{1-10}$ alkyl, $C_{1-10}$ alkylthio, phenyl, chloro, bromo, iodo, azido, nitro, $C_{1-10}$ alkoxycarbonyl-substituted phenyl, $C_{2-10}$ alkenyl, $C_{2-10}$ alkyl omega substituted with $SO_2F$, N-succinimide-O—C(O)—, methyldiaziridine, trifluoromethyldiaziridine, rhodamine, fluorescein or coumarin; aryl p-substituted with N-succinimide-O—C(O)—, rhodamine, fluorescein or coumarin, phenoxy p-substituted with N-succinimide-O—C(O)—, rhodamine, fluorescein or coumarin, and 2-(aryliodanyl)-1,1,2,2-tetrafluoroethyl; in alkyl chains, two neighboring carbon atoms may be replaced by a methylamido group (—N(Me)-C(O)—) and/or by a phenyl group.

It can be seen from the definition of the substituents that $A^1$ is a bivalent substituent, typically aliphatic or carbonyl. $A^2$ can be a monovalent substituent bound to $A^1$, or it can be bivalent substituent bound to $A^1$ or to the iodine moiety. $A^2$ is typically bound to $A^1$ via a heteroatom (O or N) or by a carbonyl (C=O) carbon.

In one preferred embodiment, $A^1$ is present, $A^2$ is a bivalent substituent, and $X^1$ is not present. In another preferred embodiment, $A^1$ is present, $A^2$ is a monovalent substituent bound to $A^1$, and $X^1$ is present.

Preferably, $X^1$ is chloro.

Preferably, $A^1$ is C=O or $-C(CH_3)_2-$, 1,1-cyclobutylene, 1,1-cyclopentylene, 1,1-cyclohexylene, 1,1-(4-oxacyclohexylene).

Preferably, $A^2$ is selected from —OH, —O—, $R^9C(O)O-$, wherein $R^9$ is selected from C110 alkyl, phenyl-substituted $C_{1-10}$ alkyl, $CH_3(OCH_2CH_2)_o-$, wherein o=1-10, $Cl^-Me_3N^+(CH_2)_p-$, wherein p=1-10, $-(CX_2)_mCOOQ$, $-(CX_2)_mSO_3Q$, wherein m=2-3, -phenyl-$SO_3Q$, -phenyl-COOQ, $-(CX_2)_mCOO-$, $-(CX_2)_mSO_3-$, wherein m=2-3, -phenyl-$SO_3-$, -phenyl-COO—, $X_2$=F or Cl, $X_3$=H, $CH_3$, F or Cl, Q is selected from lithium, sodium, potassium, rubidium, cesium, tetra (C1-C4 alkyl, phenyl, benzyl) ammonium (such as tetramethylammonium, tetraethylammonium, tetrapropylammonium, tetrabutylammonium, benzyltriethylammonium, phenyltrimethylammonium), tri (C1-C4 alkyl, phenyl, benzyl)pyridinium.

Preferably, $R_F$ is selected from trifluoromethyl, omega-azido $C_{1-10}$ alkyl-1,1,2,2-tetrafluorobut-1-yl (such as 4-azido-1,1,2,2-tetrafluorobut-1-yl), 2-(N-imidazolyl)-1,1,2,2-tetrafluoroethan-1-yl.

The term "aromatic amino acid" is intended to cover the aromatic amino acids in free form, as well as aromatic amino acids bound in peptide chains.

Aromatic amino acids include phenylalanine, tryptophan, tyrosine, histidine, thyroxine, 5-hydroxytryptophan, L-DOPA. Preferably, aromatic amino acids include phenylalanine, tryptophan, tyrosine, histidine. Most preferably, the aromatic amino acid is tryptophan.

The term "nucleobases" is intended to cover adenine, cytosine, guanine, thymine, uracil, xanthine, hypoxanthine, 7-methylguanine, any of them in free form, or in the form of nucleoside, or in the form of nucleotide, or in the form of nucleotide bound in an oligonucleotide or polynucleotide chain. Most preferably, the nucleobase is cytosine.

"Me" is intended to designate methyl group.

Within the framework of the present invention, it was surprisingly found that the reaction of the Togni-type reagent of formula I with a reductant generates the fluoroalkylating radical $R_{F\bullet}$ in an extremely fast reaction (few seconds), and the fluoroalkylating radical in turn immediately reacts with available aromatic amino acids or nucleobases. This allows to label or crosslink peptides, proteins or nucleic acid on pre-determined amino acids or nucleobases. Due to the defined preference of Togni-type reagents for certain amino acids and nucleobases which can be fine tuned by the structure of the $R_{F\bullet}$ moiety, a pre-defined reaction may be achieved with preciseness. The exceptionally high rate of fluoroalkyl radical capture by aromatic amino acid residues is advantageous.

An interesting application of the method of the present invention is a method of surface-labeling of proteins or nucleic acids which relies on the fast production of the reactive $R_{F\bullet}$ radical which immediately reacts with the amino acids or nucleobases which are present on the surface of the protein or nucleic acid. The resulting labeled protein or nucleic acid can then be imaged (e.g., when the $R_{F\bullet}$ radical bears a directly detectable group such as a fluorophore or a chromophore). Alternatively, and particularly in case of a protein, the protein can then be digested into shorter peptides or amino acids, and the labeled amino acids can then be detected by known methods.

Furthermore, the surface labelling method could be also employed for surface mapping of a protein such as an antibody, therefore constituting a protein characterisation method.

Advantageously, the said surface labelling method could be applied to isolated pure proteins, as well as to protein-protein complexes, such as antibody-antigen complexes. The solvent accessible portion of the protein-protein complex would undergo fluoroalkylation, while the portions that are solvent-inaccessible due to binding would be protected from the surface mapping. Therefore, this method also represents an epitope-binding characterisation method.

More preferably, surface fluoroalkylation of a protein with an azidofluoroalkyl probe followed by subsequent affinity enrichment (click reaction with a biotin-alkyne) can be used to enhance the sensitivity of the method and the quality of the analytical data.

Reductants are preferably selected from a group including sodium ascorbate, potassium ascorbate, calcium ascorbate, magnesium ascorbate, esters of ascorbic acid with carboxylic acids of the formula $R^{10}CO_2H$ wherein $R^{10}$ is $C_{1-18}$ alkyl; sodium sulphite, sodium dithionite, tetrakis(dimethylamino)ethylene, sodium phosphite, sodium hypophosphite, and sodium hydroxymethanesulfinate (Rongalite).

Preferred solvents for the reaction are water, aqueous buffers of pH range 4 to 10, preferably 5 to 8, dimethylsulfoxide (DMSO), acetonitrile (MeCN), dimethylformamide (DMF), dichloromethane, chloroform, methanol, and mixtures thereof.

Preferred amount of the reductant is 0.05-1.2 equivalents relative to reagent 1, preferably 0.5-1.0 equivalents, more preferably approximately stoichiometric ratio of 0.9-1.1 equivalents.

Preferred reaction conditions include the use of degassed or inert-gas purged solvents and buffers, or conducting the reaction under inert gas.

Reagents 1 in the presence of reductants decompose to form $R_{F\bullet}$ radicals (Scheme 1) which react with solvent-accessible aromatic amino acid residues, or with nucleobases, affording products of aromatic hydrogen substitution, such as:

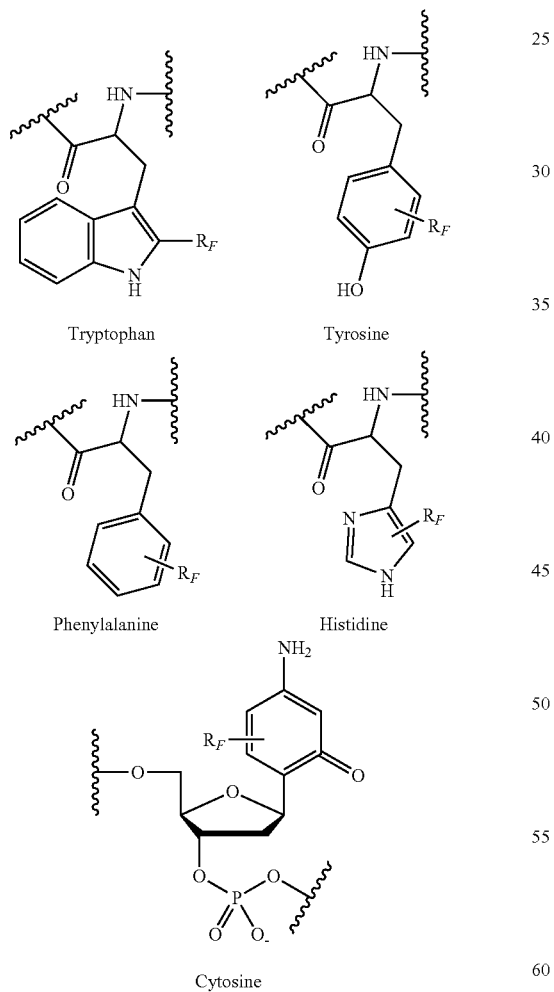

presence of the reductant extremely fast. The method of the present invention has advantage over existing methods for aromatic amino acid modification in the speed of the reactions ($R_F$ radicals are formed and react within seconds), selectivity towards the target compounds, in particular towards tryptophan or cytosine under certain conditions, high stability of conjugates and the use of inexpensive, non-toxic, transition metal-free and biocompatible reductants. Furthermore, the method enables fluoroalkylation of the aromatic amino acids present on the solvent-exposed surface of a protein, thus representing a tool for surface mapping of proteins which can find use in protein-ligand binding studies and epitope mapping studies.

Specific structures of reagents 1 used in Examples section are shown below. These reagents represent preferred embodiments of the invention.

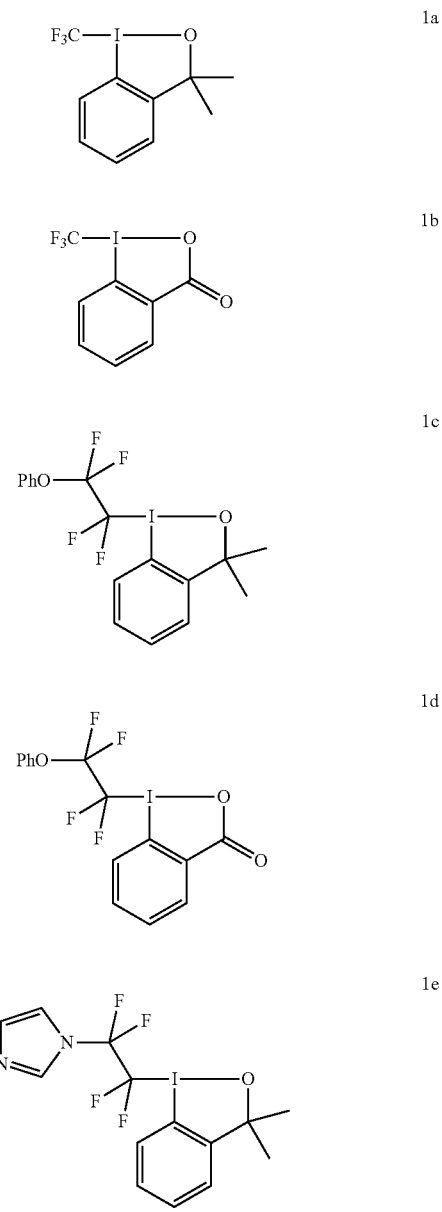

Modification of aromatic amino acids or amino acid residues in peptides or nucleobases using hypervalent iodine reagents has not been described in literature and its practical use is only made possible by the present finding that Togni-type reagents of formula I form the $R_{F\bullet}$ radicals in the -continued 1f 1g 1h 1i 1j 1k -continued 1l 1m 1n 1o 1p 1q -continued

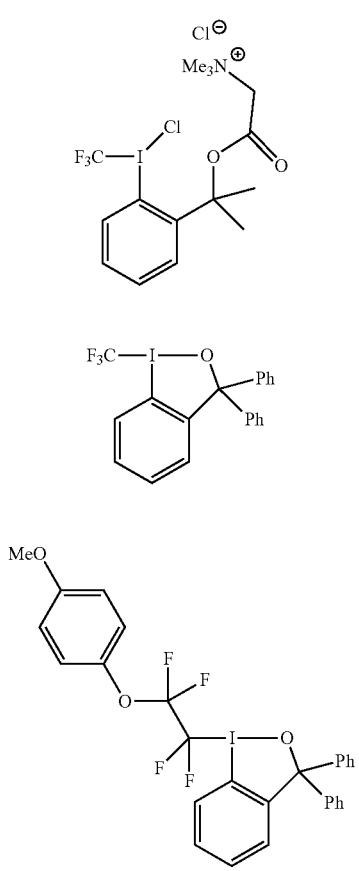

1r

1s

1t

The preferred specific structures of the reagents 1 include known compounds 1a and 1b (Eisenberger, P.; Gischig, S.; Togni, A. *Chemistry—A European Journal* 2006, 12, 2586-2579), 1c-1f (Matoušek, V.; Václavík, J.; Hájek, P.; Charpentier, J.; Blastik, Z. E.; Pietrasiak, E.; Budinská, A.; Togni, A.; Beier, P. *Chemistry—A European Journal*, 2016, 22, 417-424), 1g (Václavíc, J.; Zschoche, R.; Klimánkova, I.; Matoušek, V.; Beier, P.; Hilvert, D.; Togni, A. *Chemistry—A European Journal* 2017, 23, 6490-6494). Furthermore, an example of rhodamine-substituted Togni-type reagent and its synthesis was described in Václavík, J. et al. *Chemistry—A European Journal* 2017, 23, 6490-6494. 1i was described in *ACS Cent. Sci.* 2016, 2, 5, 341-350.

Protonation with Brønstedt acids (such as HCl), acylation with carboxylic acid chlorides or anhydrides provided activated (more electrophilic) reagents in salt or acetylated forms. Addition of LiCl led to the formation of chlorido-coordinated reagents (FIG. 1). Compounds 1h, 1j-1t are novel compounds.

The method of the present invention enables a versatile, selective, mild, fast and irreversible modification of aromatic amino acid residues in free form or bound in peptides or proteins, as well as nucleobases in free form or bound in DNA or RNA chains with fluoroalkyl-bound groups of choice. The method has the advantage of reacting with all aromatic amino acids, with high selectivity to tryptophan; and with all nucleobases, with selectivity to cytosine.

Additionally, novel hypervalent iodine fluoroalkyl reagents of general formula 1-1 are claimed (1-1)

wherein
$R^1$ is selected from H, C1-C4 alkyl, $Me(OCH_2CH_2)_nO$, wherein n=1-10,
$X^1$ is not present or is selected from chloride, tetrafluoroborate, hexafluorophosphate, trifluoromethanesulfonate, methanesulfonate, toluenesulfonate, fluoride, bromide, $(F(CF_2)_sSO_2)_2N$, wherein s=1 to 4, C1-C6 carboxylate, fluorinated C1-C6 carboxylate, hexafluoroantimonate;
$A^1$ is not present or is selected from
  carbonyl group (C=O),
  $R^2$—C—$R^3$, where $R^2$ and $R^3$ are independently selected from fluorine, chlorine, hydrogen, $CF_3$, $C_1$-$C_4$ alkyl, phenyl, phenyl substituted by fluorine, chlorine and/or $C_1$-$C_4$ alkyl, omega-methoxy-($C_1$-$C_4$)alkyl; or $R^2$ and $R^3$ together with the carbon atom to which they are bound form 1,1-cyclobutylene, 1,1-cyclopentylene, 1,1-cyclohexylene, 1,1-(4-oxa-cyclohexylene);
$A^2$ is not present or is selected from
  hydroxyl group (OH),
  oxygen (—O—),
  $C_{1-4}$ alkoxy,
  $OSiR^4R^5R^6$, wherein $R^4,R^5,R^6$ are independently selected from methyl, ethyl, n-propyl, i-propyl and phenyl;
  $R^7N$, wherein $R^7$ is selected from $C_{1-10}$ alkyl, phenyl-substituted $C_{1-10}$ alkyl, 4-chlorophenyl-substituted $C_{1-10}$ alkyl, and $CH_3(OCH_2CH_2)_n$;
  $R^8CO$—, wherein $R^8$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_mCOOQ$, —$(CX_2)_m$ $SO_3Q$, wherein m=2-3, -phenyl-$SO_3Q$, -phenyl-COOQ, —$(CX_2)_m$COO—, —$(CX_2)_mSO_3$—, wherein m=2-3, -phenyl-$SO_3$—, -phenyl-COO—,
  $X_2$=F or Cl, $X_3$=H, $CH_3$, F or Cl,
  Q is selected from lithium, sodium, potassium, rubidium, cesium, tetra (C1-C4 alkyl, phenyl, benzyl) ammonium, tri (C1-C4 alkyl, phenyl, benzyl) pyridinium;
  $R^9C(O)O$—, wherein $R^9$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_mCOOQ$, —$(CX_2)_m$ $SO_3Q$, wherein m=2-3, -phenyl-$SO_3Q$, -phenyl-COOQ, —$(CX_2)_m$COO—, —$(CX_2)_mSO_3$—, wherein m=2-3, -phenyl-$SO_3$—, -phenyl-COO—,
  $X_2$=F or Cl, $X_3$=H, $CH_3$, F or Cl,
  Q is selected from lithium, sodium, potassium, rubidium, cesium, tetra (C1-C4 alkyl, phenyl, benzyl) ammonium, tri (C1-C4 alkyl, phenyl, benzyl) pyridinium;

$R_F$ is —$CF_2$-$A^3$-$A^4$, wherein
  $A^3$ is not present and $A^4$ is fluorine, or phenylsulfanyl (PhS) group, or
  $A^3$ is $CF_2$ and $A^4$ is fluorine, $C_{1-10}$ perfluoroalkyl, phenoxy, $C_{1-10}$ alkoxy, phenylsulfanyl, N-imidazolyl, N-pyrazolyl, N-benzimidazolyl, N-triazoyl, N-(2-methyl)imidazolyl, $CH_3(OCH_2CH_2)$—O, where n=1-10, $Cl^-MeH_2N^+(CH_2)_m$ wherein r=1-10, $Cl^-MeH_2N^+(CH_2)_2$-phenyloxy, $C_{1-10}$ alkyl, ethenyl, ethynyl, omega-azido $C_{1-10}$ alkyl, omega-amino $C_{1-10}$ alkyl, omega-ethynyl $C_{1-10}$ alkyl, $C_{1-10}$ alkylthio, phenyl, chloro, bromo, iodo, azido, nitro, $C_{1-10}$ alkoxycarbonyl-substituted phenyl, $C_{2-10}$ alkenyl, $C_{2-10}$ alkyl omega substituted with $SO_2F$, N-succinimide-O—C(O)—, methyldiaziridine, trifluoromethyldiaziridine, rhodamine, fluorescein or coumarin; aryl p-substituted with N-succinimide-O—C(O)—, rhodamine, fluorescein or coumarin, phenoxy p-substituted with N-succinimide-O—C(O)—, rhodamine, fluorescein or coumarin, and 2-(aryliodanyl)-1,1,2,2-tetrafluoroethyl; in alkyl chains, two neighboring carbon atoms may be replaced by a methylamido group (—N(Me)-C(O)—) and/or by a phenyl group,
provided that:
  A2 is not —O— or —OH, when: A1 is C=O or $R^2$—C—$R^3$, wherein $R^2$ and $R^3$ are methyls;
  A2 is not —O—C(=O)$CH_3$, when: $R_F$ is $CF_3$ and A1 is C=O or $R^2$—C—$R^3$, wherein $R^2$ and $R^3$ are methyls;
  A2 is not —O— or —OH, when: $X^1$ is not present, $R_F$ is $CF_3$ and A1 is $R^2$—C—$R^3$, wherein $R^2$ and $R^3$ are selected from alkyl and $CF_3$ or wherein $R^2$ is methyl and $R^3$ is phenyl or $R^2$ and $R^3$ together form 1,1-cyclohexylene;
  A2 is not —O— or —OH, when: $X^1$ is not present, $R_F$ is selected from perfluoroethyl, perfluoropropyl, perfluorobutyl, perfluorohexyl or perfluorooctyl, A1 is $R^2$—C—$R^3$, wherein $R^2$ is methyl and $R^3$ is phenyl or isopropyl;
  A2 is not $R^7N$, wherein $R^7$ is selected from $C_{1-10}$ alkyl, phenyl-substituted $C_{1-10}$ alkyl, when: $X^1$ is not present, $R_F$ is $CF_3$ and A1 is C=O.

List of Abbreviations

Ac acetyl
br s broad signal
d doublet
DBCO dibenzocyclooctyne
DCM dichloromethane
DMF dimethylformamide
DMSO dimethylsulfoxid
DTT 1,4-dithiothreitol
equiv. equivalent(s)
Et ethyl
ESI electrospray ionization
FDR false discovery rate
FT-ICR Fourier-transform ion cyclotron resonance
hCa Human Carbonic Anhydrase
HCD Higher-energy C-trap dissociation
HEPES 4-(2-hydroxyethyl)piperazine-1-ethanesulfonic acid
HRMS high-resolution mass spectroscopy
HSQC heteronuclear single quantum coherence
ID internal diameter
LC liquid chromatography
LDS lithium dodecyl sulfate
m multiplet
MALDI matrix-assisted laser desorption ionization
Me methyl
MES 2-(N-morpholino)ethanesulfonic acid
mol. Molar
m.p. melting point
MS mass spectroscopy
NMR nuclear magnetic resonance
p pentet
q quartet
$R_f$ retention factor
s singlet
ssDNA single-stranded deoxyribonucleic acid
t triplet
TBAT tetrabutylammonium triphenyldifluorosilicate
t-Bu tertiary butyl
TFA trifluoroacetic acid
TRIS tris(hydroxymethyl)aminomethane

EXAMPLES

Figure 1:
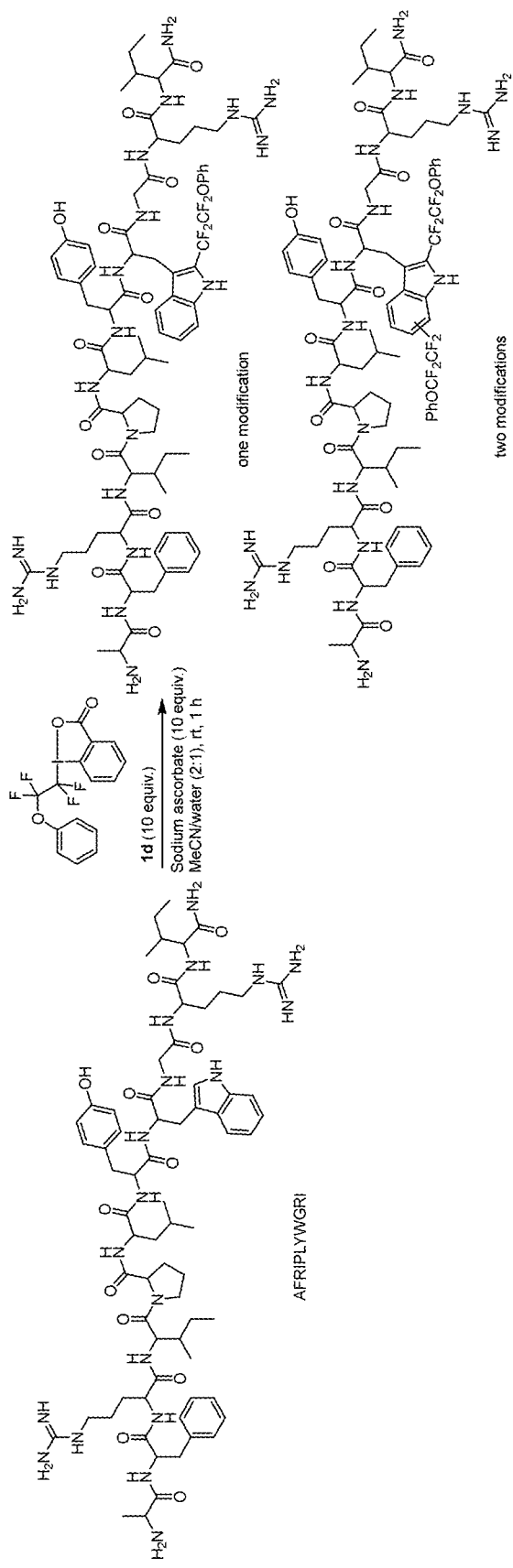
FIG. 1: Fluoroalkylation of peptide AFRIPLYWGRI.

The subject-matter of present invention is further illustrated by the following examples which should not be construed as limiting the scope of the invention.

Scheme 1 generally shows the reaction scheme for preparation of individual reagents as described in the following examples.

Scheme 1
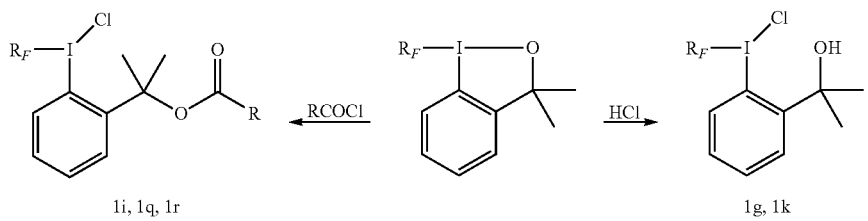
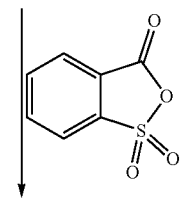
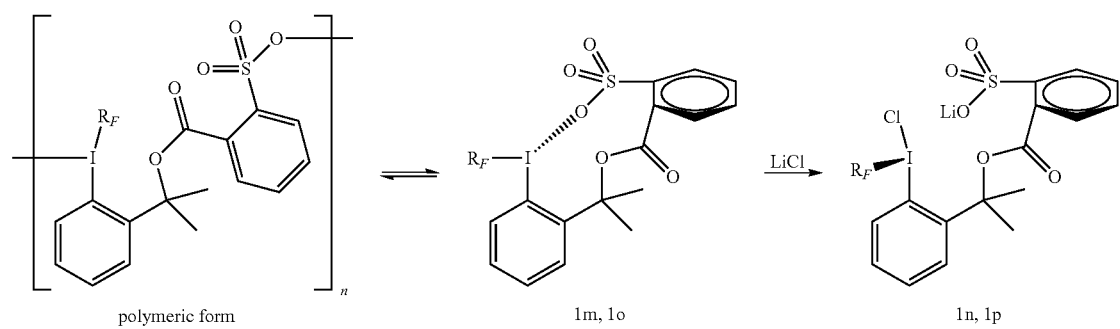
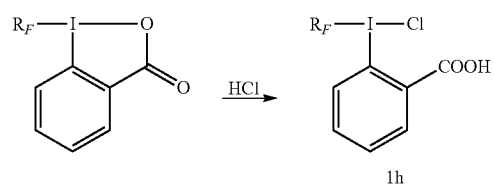

Example 1: Synthesis of Reagent 1h

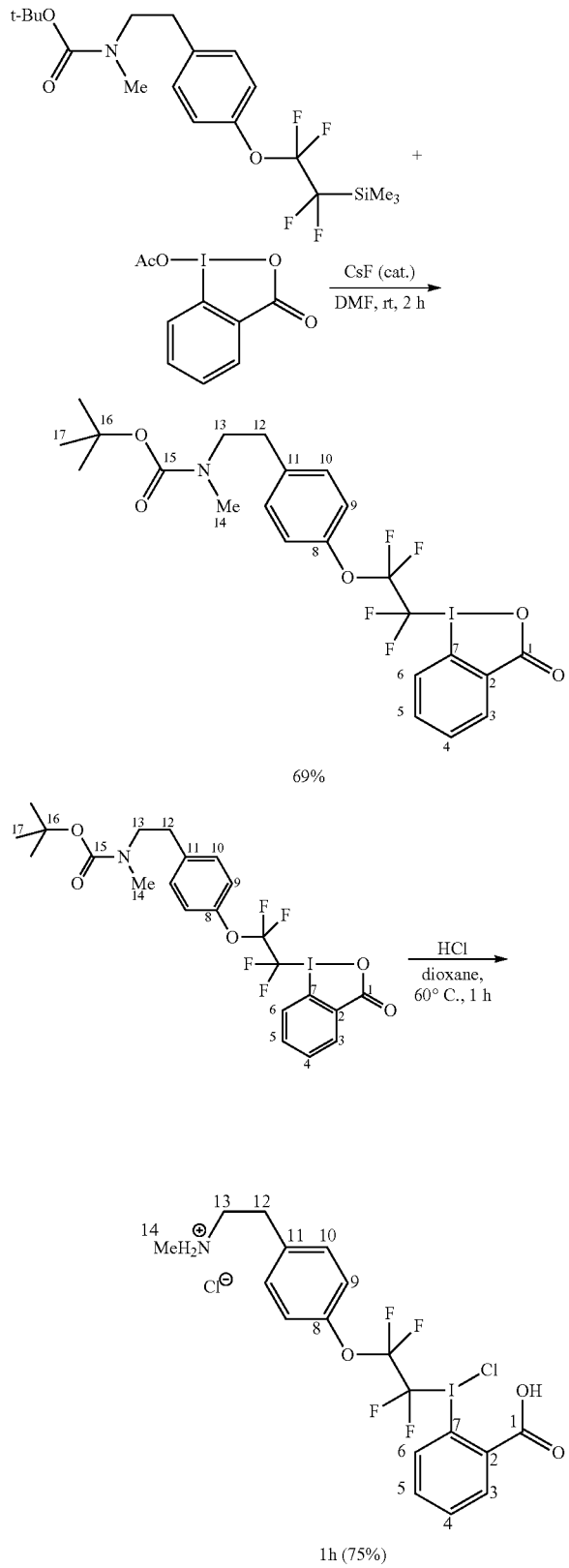

Step 1: CsF (0.45 mmol, 68 mg) and 3-oxo-1λ³-benzo[d][1,2]iodaoxol-1(3H)-yl acetate (3 mmol, 918 mg) were dissolved in dry DMF (2.5 ml) under argon atmosphere. To the well stirred suspension, solution of tert-butyl methyl(4-(1,1,2,2-tetrafluoro-2-(trimethylsilyl)ethoxy)-phenethyl)carbamate (1.5 mmol, 635 mg) in dry DMF (5 ml) was added dropwise. After 2 hours, the reaction mixture was diluted with EtOAc (50 ml), washed with water (10 ml), 1 M $NaHCO_3$ (2×10 ml), 1 M LiCl (2×10 ml), dried over $MgSO_4$, filtered and concentrated under reduced pressure. The crude product was purified by filtration through a pad of alumina (20 g). The impurities were washed away with $Et_2O$ (150 ml) and the alumina-adsorbed title product was completely eluted using MeOH (75 ml). The pure intermediate was obtained after concentration under reduced pressure as a colorless oil. Yield: 604 mg (69%); $^1H$ NMR (401.00 MHz, $CDCl_3$): δ 1.34-1.39 (bs, 9H, C(17)$H_3$), 2.76-2.83 (bm, 5H, C(12)$H_2$ and C(14)$H_3$), 3.41 (t, $^3J_{HH}$=7.2 Hz, 2H, C(13)$H_2$), 7.12 (d, $^3J_{HH}$=8.2 Hz, 2H, C(9)H or C(10)H), 7.16-7.25 (bm, 2H, C(9)H or C(10)H), 7.66-7.80 (m, 2H, C(4)H and C(5)H), 7.90 (d, $^3J_{HH}$=8.1 Hz, 1H, C(6)H), 8.43 (dd, $^3J_{HH}$=7.3 Hz, $^4J_{HH}$=2.1 Hz, 1H, C(3)H); $^{19}F$ NMR (377.28 MHz, $CDCl_3$): δ -89.5 (bs, 2F, $CF_2$), -84.4 (bs, 2F, $CF_2$); $^{13}C$ {$^1H$} NMR (100.84 MHz, $CDCl_3$): δ 28.2 (s, 1C, C(17)$H_3$), 33.3 and 33.7 (s, 1C, C(12)$H_2$), 34.1 and 34.6 (s, 1C, C(14)$H_3$), 49.9 and 50.4 (s, 1C, C(13)$H_2$), 79.3 (s, 1C, C(16)), 110.5 (tt, $^1J_{CF}$=335.4 Hz, $^2J_{CF}$=40.0 Hz, 1C, $CF_2$), 114.8 (s, 1C, C(7)), 117.2 (tt, $^1J_{CF}$=277.9 Hz, $^2J_{CF}$=25.6 Hz, 1C, $CF_2$), 121.4 (bs, 2C, C(9)H or C(10)H), 128.1 (t, $^4J_{CF}$=5.7 Hz, 1C, C(6)H), 130.3 (s, 2C, C(9)H or C(10)H), 131.5 (s, 1C, C(2)), 132.3 (s, 1C, C(4)), 133.7 (s, 1C, C(3)H), 135.2 (s, 1C, C(5)), 138.8 (m, 1C, C(11)), 146.4 (s, 1C, C(8)), 155.4 (s, 1C, C(15)), 165.9 (s, 1C, C(1)); HRMS (m/z, $ESI^+$): $[M+Na]^+$ calc. for $C_{23}H_{24}F_4INO_5Na$, 620.0528, found, 620.0530.

Step 2: The iodane intermediate (3.4 mmol, 2 g) was dissolved in 1,2-dichloroethane (68 ml) in a round bottom flask. HCl (4 M in dioxane, 34 mmol, 8.5 ml) was added and the resulting mixture was stirred for 1 hour at 60° C. The solvent was evaporated, leading to formation of white particles which were subsequently suspended in $Et_2O$. The mother liquor was decanted and pure 1h was obtained as a white solid. Yield: 1.46 g (75%); m.p. 120-123° C.; $^1H$ NMR (401.00 MHz, DMSO-$d_6$): δ 2.54 (t, $^3J_{HH}$=5.3 Hz, 3H, C(14)$H_3$), 2.98-3.01 (bm, 2H, C(12)$H_2$, 3.06-3.21 (bm, 2H, C(13)$H_2$), 7.25 (d, $^3J_{HH}$=8.0 Hz, 2H, C(9)H), 7.37 (d, $^3J_{HH}$=8.0 Hz, 2H, C(10)H), 7.70 (t, $^3J_{HH}$=7.6 Hz, 1H, C(5)H), 7.82 (t, $^3J_{HH}$=7.5 Hz, 1H, C(4)H), 8.24 (d, $^3J_{HH}$=7.6 Hz, 1H, C(6)H), 8.49 (d, $^3J_{HH}$=7.6 Hz, 1H, C(3)H), 9.17 (s, 2H, $NH_2$); $^{19}F$ NMR (377.28 MHz, DMSO-$d_6$): δ -88.5 (bs, 2F, $CF_2$), -82.9 (t, $^3J_{FF}$=6.6 Hz, 2F, $CF_2$); $^{13}C$ {$^1H$} NMR (100.84 MHz, DMSO-$d_6$): δ 31.1 (s, 1C, C(12)$H_2$), 32.8 (s, 1C, C(14)$H_3$), 49.3 (s, 1C, C(13)$H_2$), 112.2 (tt, $^1J_{CF}$=341.8 Hz, $^2J_{CF}$=41.2 Hz, 1C, $CF_2$), 116.9 (tt, $^1J_{CF}$=275.5 Hz, $^2J_{CF}$=26.9 Hz, 1C, $CF_2$), 119.7 (s, 1C, C(7)), 121.5 (bs, 2C, C(9)H), 130.8 (s, 2C, C(10)H), 131.1 (s, 1C, C(2)), 132.2 (s, 1C, C(6)H), 133.1 (s, 1C, C(4)H), 135.5 (s, 1C, C(5)H), 137.0 (m, C(8)), 140.0 (s, C(3)H), 147.1 (s, C(11)), 165.5 (s, C(1)); HRMS (m/z, $ESI^+$): $[M+H]^+$ calc. for $C_{18}H_{17}F_4INO_3$, 498.0184, found, 498.0183.

Example 2: Synthesis of Reagent 1i

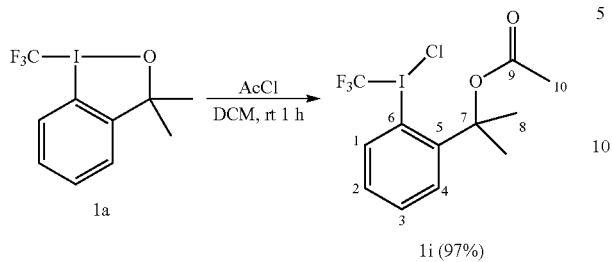

1a (0.5 mmol, 165 mg) was dissolved in dry DCM (1 ml) and acetyl chloride (0.75 mmol, 0.06 ml) was added in one portion. The mixture was stirred 15 minutes at laboratory temperature. After that volatiles were removed under reduced pressure and the obtained particles were washed with pentane to give pure 1i as a white solid. Yield: 198 mg (97%); $^1$H NMR (401.00 MHz, CDCl$_3$): δ 2.05 (s, 6H, C(8)H$_3$), 2.19 (s, 3H, C(10)H$_3$), 7.34 (ddd, $^3J_{HH}$=7.9 Hz, $^3J_{HH}$=6.5 Hz, $^4J_{HH}$=2.6 Hz, 1H, C(3)H), 7.60-7.73 (m, 2H, C(2)H and C(4)H), 8.38 (dd, $^3J_{HH}$=7.8 Hz, $^4J_{HH}$=1.1 Hz, 1H, C(1)H); $^{19}$F NMR (377.28 MHz, CDCl$_3$): δ −32.7 (s, 3F, CF$_3$); $^{13}$C {$^1$H} NMR (100.84 MHz, CDCl$_3$): δ 22.9 (s, 1C, C(10)H$_3$), 28.6 (s, 2C, C(8)H$_3$), 82.4 (s, 1C, C(7)), 107.8 (q, $^1J_{CF}$=388.6 Hz, 1C, CF$_3$), 116.3 (s, 1C, C(6)), 129.1 (s, 1C, C(4)H), 131.1 (s, 1C, C(3)H), 133.2 (s, 1C, C(2)H), 141.7 (s, 1C, C(1)), 145.9 (s, 1C, C(5)), 169.5 (s, 1C, C(9)); HRMS (m/z, ESI$^+$): [M+Na]$^+$ calc. for C$_{12}$H$_{13}$O$_2$ClF$_3$INa, 430.9493, found, 430.9489.

Example 3: Synthesis of Reagent 1j and 1k

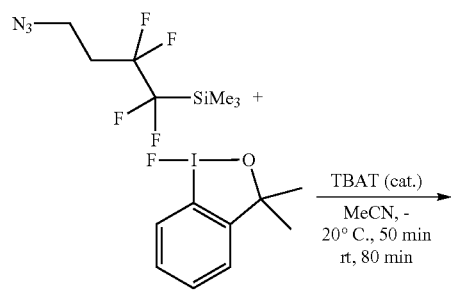

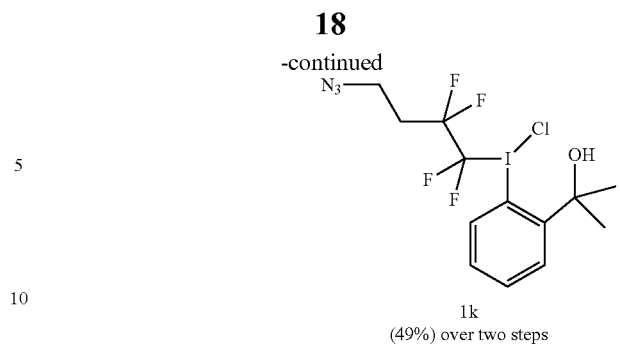

1-Fluoro-3,3-dimethyl-1,3-dihydro-1λ$^3$-benzo[d][1,2]iodaoxole (1.83 g, 6.41 mmol, 1.3 equiv.) was dissolved in MeCN (15 ml) and to the resulting solution was added TBAT (133 mg, 0.247 mmol, 0.05 equiv.) The reaction mixture was cooled to −20° C. and a solution of 4-azido-1-trimethylsilyl-1,1,2,2-tetrafluorobutane (1.5 g of 80% purity, 4.93 mmol, 1 equiv.) in MeCN (10 ml) was slowly introduced to the reaction mixture within 50 minutes. After the addition was complete, the reaction mixture was gradually warmed to room temperature within 80 minutes. The resulting brownish solution was evaporated to dryness under reduced pressure and the resulting viscous oil was redissolved in cyclohexane (35 ml). The solution was filtered through a pad of alumina (activated by heatgun drying in vacuo) and evaporated to dryness under reduced pressure. The resulting liquid was dissolved in a mixture of Et$_2$O (3 ml) and pentane (7 ml), the solution was cooled to 0° C. and HCl in Et$_2$O (3.3 ml of 3M solution, 9.86 mmol, 2 equiv) was slowly added. The resulting white solid was filtered off, washed with pentane and dried in vacuo. Yield: 0.97 g (49%). $^1$H NMR (401 MHz, CDCl$_3$): δ 1.72 (s, 6H, CH$_3$), 2.30-2.43 (m, 2H, CH$_2$CF$_2$), 3.59 (t, J=7.0 Hz, 2H, CH$_2$N$_3$), 4.56 (br s, 1H, OH), 7.25-7.29 (m, 1H, C$_{Ar}$H), 7.59-7.66 (m, 2H, C$_{Ar}$H), 8.13 (d, J=8.1 Hz, 1H, C$_{Ar}$H); $^{19}$F NMR (377 MHz, CDCl$_3$) δ −80.6 (s, 2F, CF$_2$), −106.4 (t, J=18.2 Hz, 2F, CF$_2$); $^{13}$C NMR (100.8 Hz, CDCl$_3$) δ 29.6 (t, $^2J_{CF}$=22.4 Hz, CH$_2$CF$_2$), 31.9 (CH$_3$), 43.4 (t, $^3J_{CF}$=3.8 Hz, CH$_2$N$_3$), 74.2 (C—OH), 112.8 (C—I), 112.0-119.3 (m, CF$_2$), 129.8, 130.1, 132.8, 139.2, 147.3; HRMS (m/z, ESI$^+$): [M]$^+$ calc. for C$_{13}$H$_{15}$ON$_3$F$_4$I, 432.01904, found, 432.01924.

Example 4: Synthesis of Reagent 1l

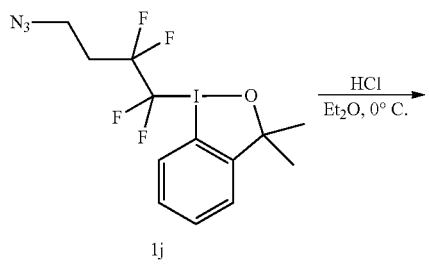

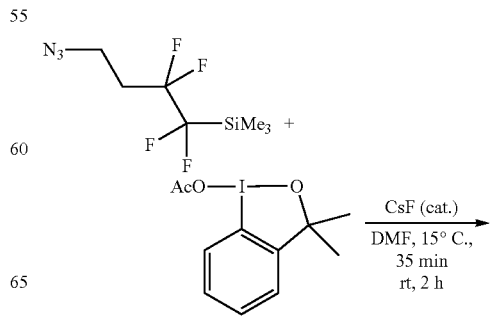

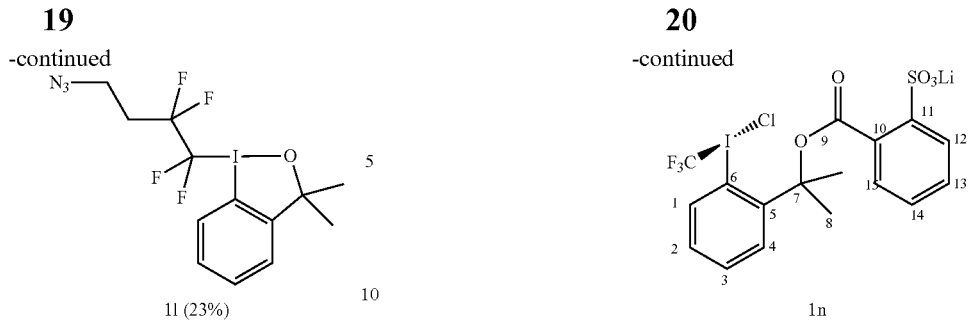

11 (23%)

CsF (120 mg, 0.822 mmol, 0.1 equiv.) was dried with a heat gun under vacuum and then suspended under Ar together with 1-acetoxy-1λ$^3$-benzo[d][1,2]iodaoxol-3(1H)-one (5.03 g, 16.44 mmol, 2 equiv.) in DMF (30 ml). The reaction mixture was cooled to 15° C. and a solution of 4-azido-1-trimethylsilyl-1,1,2,2-tetrafluorobutane (2.5 g in 80% purity, 8.22 mmol, 1 equiv.) in dry DMF (10 ml) was gradually added over the course of 35 minutes. After that, the resulting mixture was left to react while reaching ambient temperature (2 h). Then it was poured into cold dilute solution of NaHCO$_3$ (250 ml, 5% w/w) and stirred for 10 min to bring about complete hydrolysis of the acetoxyiodane precursor to the insoluble hydroxy derivative. EtOAc (300 ml) was added, then the biphasic mixture was stirred and subsequently filtered through a pad of Celite. The organic phase was separated and the aqueous phase was extracted with additional EtOAc. The combined organic phases were washed twice with 5% solution of LiCl (2×100 ml). The organic phase was dried over Na$_2$SO$_4$ and concentrated to near dryness. The precipitated product was cooled to 0° C., suspended in cold Et$_2$O (3 ml), filtered off, washed twice with cold Et$_2$O (2×5 ml) and finally dried in high vacuum. Yield: 0.63 g (23%); $^1$H NMR (300 MHz, CDCl$_3$, 25° C.) 2.65-2.37 (m, 2H), 3.70 (t, J=7.0 Hz, 2H), 7.77 (dd, J=11.0, 5.8 Hz, 3H), δ 8.54-8.40 (m, 1H); $^{19}$F NMR (282 MHz, CDCl$_3$) δ −85.70 (s), −105.85 (t, J=18.3 Hz).

Example 5: Synthesis of Reagents 1m and 1n

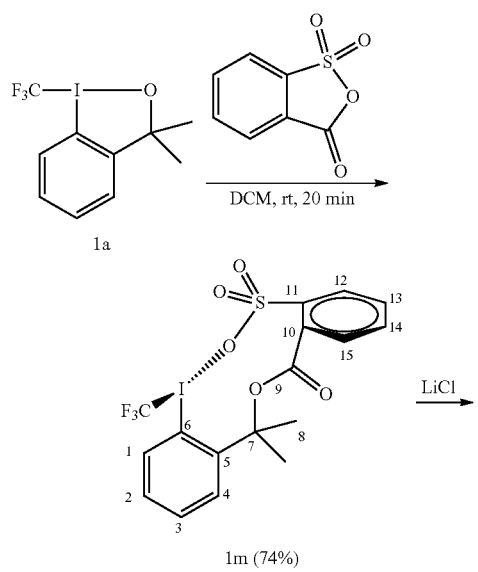

1m (74%)

2,1-Benzoxathiol-3-one-1,1-dioxide (184 mg, 1 mmol) was dissolved in dry DCM (5 ml) under argon atmosphere and 1a (330 mg, 1 mmol) was added in one portion. The mixture was stirred 20 minutes at room temperature. After that, the volatiles were removed under reduced pressure and the obtained particles were washed with Et$_2$O (5 ml) to give pure 1m as a white solid. Yield: 383 mg (74%); $^1$H NMR (600.13 MHz, DMSO-d$_6$): δ 1.99 (bs, 6H, C(8)H$_3$), 7.38 (dd, $^3J_{HH}$=7.2 Hz, $^4J_{HH}$=1.8 Hz, 1H, C(15)H), 7.53-7.58 (m, 3H, C(3)H, C(13)H, and C(14)H), 7.73 (dd, $^3J_{HH}$=7.2 Hz, $^4J_{HH}$=1.9 Hz, 1H, C(12)H), 7.85 (td, $^3J_{HH}$=7.6 Hz, $^4J_{HH}$=1.3 Hz, 1H, C(2)H), 7.95 (dd, $^3J_{HH}$=8.0 Hz, $^4J_{HH}$=1.7 Hz, 1H, C(4)H), 8.75 (dd, $^3J_{HH}$=7.9 Hz, $^4J_{HH}$=1.3 Hz, 1H, C(1)H); $^{19}$F NMR (377.28 MHz, DMSO-d$_6$): δ −28.6 (s, 3F, CF$_3$); $^{13}$C CHI NMR (150.92 MHz, DMSO-d$_6$): δ 31.0 (only in HSQC, 2C, C(8)H$_3$), 81.7 (s, 1C, C(7)), 100.1 (q, $^1J_{CF}$=367.8 Hz, 1C, CF$_3$), 115.2 (s, 1C, C(6)), 126.6 (s, 1C, C(15)H), 127.2 (s, 1C, C(12)H), 129.2 (s, 1C, C(4)H), 129.8 (s, 1C, C(13)H or C(14)H), 130.1 (s, 1C, C(13)H or C(14)H), 130.7 (s, 1C, C(11)), 131.2 (s, 1C, C(3)H), 133.5 (s, 1C, C(2)H), 140.7 (s, 1C, C(10)), 141.7 (s, 1C, C(1)), 144.5 (s, 1C, C(5)), 166.4 (s, 1C, C(9)); HRMS (m/z, ESI$^+$): [M+Na]$^+$ calc. for C$_{17}$H$_{14}$O$_5$SF$_3$INa 536.9451, found, 536.9445.

In NMR tube, 1m (10 mg, 0.02 mmol) was dissolved in DMSO-d$_6$ (0.4 ml). To the solution was added LiCl (5.8 mg, 0.12 mmol) and after 30 minutes, $^1$H and $^{19}$F NMR spectra were measured. $^1$H NMR (401.00 MHz, DMSO-d$_6$): δ 2.06 (bs, 6H, C(8)H$_3$), 7.32-7.35 (m, 2H, C(3)H and C(15)H), 7.38-7.49 (m, 2H, C(13)H and C(14)H), 7.67 (t, $^3J_{HH}$=7.6 Hz, 1H, C(2)H), 7.75 (d, $^3J_{HH}$=7.5 Hz, 1H, C(12)H), 7.92 (d, $^3J_{HH}$=8.0 Hz, 1H, C(4)H), 8.40 (d, $^3J_{HH}$=7.7 Hz, 1H, C(1)H); $^{19}$F NMR (377.28 MHz, DMSO-d$_6$): δ −33.4 (s, 3F, CF$_3$); $^{13}$C {$^1$H} NMR (100.84 MHz, DMSO-d$_6$): δ 29.1 (only in HSQC, 2C, C(8)H$_3$), 83.6 (s, 1C, C(7)), 121.3 (s, 1C, C(6)), 127.3 (s, 1C, C(15)H), 127.9 (s, 1C, C(12)H), 129.2 (s, 1C, C(4)H), 129.2 (s, 1C, C(13)H or C(14)H), 129.5 (s, 1C, C(13)H or C(14)H), 130.5 (s, 1C, C(3)H), 132.3 (s, 1C, C(11)H), 132.5 (s, 1C, C(2)H), 141.3 (s, 1C, C(1)), 144.8 (s, 1C, C(10)), 146.4 (s, 1C, C(5)), 167.3 (s, 1C, C(9)).

Example 6: Synthesis of Reagents 1o and 1p

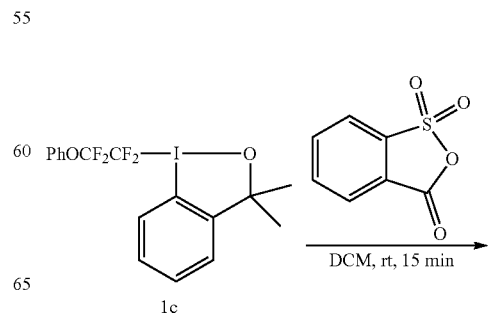

1c

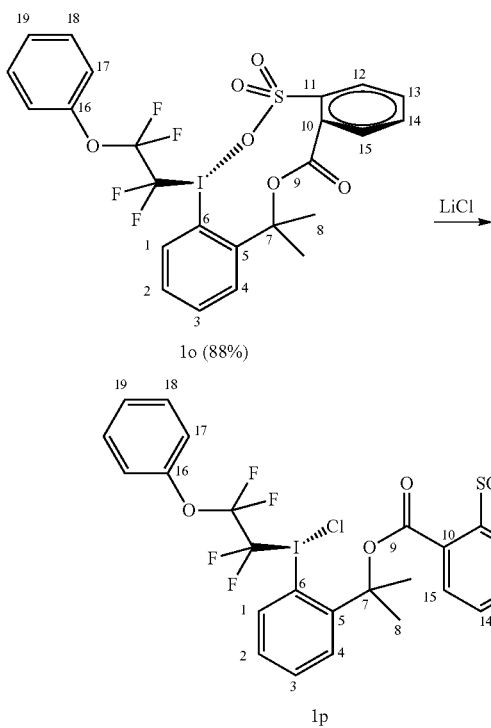

1o (88%)

1p 1c (227 mg, 0.5 mmol) was dissolved in dry DCM (2.5 ml) under argon atmosphere and 2,1-benzoxathiol-3-one-1,1-dioxide (92 mg, 0.5 mmol) was added in one portion. The mixture was stirred 15 minutes at laboratory temperature. After that volatiles were removed under reduced pressure and crude product was precipitated from DCM/Et$_2$O mixture to obtain pure 1o as white particles. Yield: 282 mg (88%); $^1$H NMR (401.00 MHz, CDCl$_3$): δ 2.08 (s, 6H, C(8)H$_3$), 7.19-7.29 (m, 3H, C(15)H and C(17)H), 7.34 (t, $^3J_{HH}$=7.4 Hz, 1H, C (19)H), 7.38-7.52 (m, 5H, C(3)H, C(13)H, C(14)H, and C(18)H), 7.80 (t, $^3J_{HH}$=7.6 Hz, 1H, C (2)H), 7.94 (dd, $^3J_{HH}$=8.0 Hz, $^4J_{HH}$=1.7 Hz 1H, C (4)H), 7.99 (d, $^3J_{HH}$=7.7 Hz, 1H, C(12)H), 8.29 (d, $^3J_{HH}$=8.0 Hz, 1H, C(1)H); $^1$H NMR (401.00 MHz, DMSO-d$_6$): δ 2.04 (s, 6H, C(8)H$_3$), 7.31-7.43 (m, 4H, C(15)H, C(17)H and C(19)H), 7.49-7.59 (m, 5H, C(3)H, C(13)H, C(14)H, and C(18)H), 7.76 (dd, $^3J_{HH}$=7.1 Hz, $^4J_{HH}$=2.0 Hz, 1H, C(12)H), 7.85 (td, $^3J_{HH}$=7.7 Hz, $^4J_{HH}$=1.3 Hz, 1H, C (2)H), 7.97 (dd, $^3J_{HH}$=8.0 Hz, $^4J_{HH}$, 1.7 Hz, 1H, C(4)H), 8.59 (d, $^3J_{HH}$=8.0 Hz, 1H, C(1)H); $^1$H NMR (401.00 MHz, CD$_3$CN): δ 2.07 (s, 6H, C(8)H$_3$), 7.27-7.44 (m, 4H, C(15)H, C(17)H and C(19)H), 7.44-7.62 (m, 5H, C(3)H, C(13)H, C(14)H, and C(18)H), 7.78-7.83 (m, 1H, C(12)H), 7.90 (td, $^3J_{HH}$=7.7 Hz, $^4J_{HH}$=1.3 Hz, 1H, C (2)H), 8.03 (dd, $^3J_{HH}$=8.0 Hz, $^4J_{HH}$=1.8 Hz, 1H, C(4)H), 8.51 (dd, $^3J_{HH}$=8.0 Hz, $^4J_{HH}$=1.3 Hz, 1H, C(1)H); $^{19}$F NMR (377.28 MHz, CDCl$_3$): δ -84.9 (t, $^3J_{FF}$=8.2 Hz, 2F, CF$_2$O), -81.5 (s, 2F, CF$_2$I); $^{19}$F NMR (377.28 MHz, DMSO-d$_6$): δ -80.5 (t, $^3J_{FF}$=6.5 Hz, 2F, CF$_2$O), -78.7 (bs, 2F, CF$_2$I); $^{19}$F NMR (377.28 MHz, CD$_3$CN): δ -84.1 (t, $^3J_{FF}$=7.4 Hz, 2F, CF$_2$O), -80.4 (t, $^3J_{FF}$=7.4 Hz, 2F, CF$_2$I); $^{13}$C {$^1$H} NMR (100.84 MHz, CDCl$_3$): δ 28.5 (s, 2C, C(8)H$_3$), 81.2 (s, 1C, C(7)), 108.5 tt, $^1J_{CF}$=279.1 Hz, $^2J_{CF}$=25.8 Hz, 1C, ICF$_2$), 109.7 (s, 1C, C(6)), 115.6 (tt, $^1J_{CF}$=337.6 Hz, $^2J_{CF}$=41.1 Hz, 1C, OCF$_2$), 121.3 (s, 2C, C(17)H), 126.4 (s, 1C, C(15)H), 127.7 (s, 1C, C(19)H), 127.8 (s, 1C, C(12)H), 130.0 (s, 1C, C(4)H), 130.0 (s, 1C, C(13)H or C(14)H), 130.2 (s, 2C, C(18)H), 130.3 (s, 1C, C(11)H), 131.1 (s, 1C, C(13)H or C(14)H), 131.6 (s, 1C, C(3)H), 134.3 (s, 1C, C(2)H), 140.0 (s, 1C, C(10)), 141.8 (s, 1C, C(1)), 146.0 (s, 1C, C(5)), 147.8 ((s, 1C, C(16)), 167.3 (s, 1C, C(9)); HRMS (m/z, ESI$^+$): [M+Na]$^+$ calc. for C$_{24}$H$_{19}$O$_6$SF$_4$INa 660.9775, found, 660.9768.

In NMR tube, 1o (23 mg, 35 μmol) was dissolved in DMSO-d$_6$ (0.4 ml). To solution was added LiCl (4.2 mg, 0.1 mmol) and after 30 minutes was measured $^1$H and $^{19}$F NMR. $^1$H NMR (401.00 MHz, DMSO-d$_6$): δ 2.12 (bs, 6H, C(8)H$_3$), 7.31-7.54 (m, 9H, C(3)H, C(13)H, C(14)H, C(15)H, C(17)H, C(18)H) and C(19)), 7.69-7.80 (m, 2H, C (2)H and C(12)H), 8.02 (dd, $^3J_{HH}$=8.1 Hz, $^4J_{HH}$=1.7 Hz, 1H, C(4)H), 8.44 (d, $^3J_{HH}$=7.9 Hz, 1H, C(1)H); $^{19}$F NMR (377.28 MHz, DMSO-d$_6$): δ -86.7 (bs, 1F, CF$_2$I), -83.8 (bs, 1F, CF$_2$I), -81.5 (t, $^3J_{FF}$=6.3 Hz, 2F, CF$_2$O); $^{13}$C {$^1$H} NMR (100.84 MHz, DMSO-d$_6$): δ 28.5 (only in HSQC, 2C, C(8)H$_3$), 83.1 (s, 1C, C(7)), 111.2 (tt, $^1J_{CF}$=344.3 Hz, $^2J_{CF}$=40.8 Hz, 1C, CF$_2$), 115.2 (s, 1C, C(6)), 116.3 (tt, $^1J_{CF}$=275.6 Hz, $^2J_{CF}$=26.5 Hz, 1C, CF$_2$), 121.8 (s, 2C, C(17)H), 126.9 (s, 1C, C(15)H), 127.4 (s, 1C, C(19)H), 127.5 (s, 1C, C(12)H), 128.7 (s, 1C, C(13)H or C(14)H), 129.1 (s, 1C, C(4)H), 129.6 (s, 1C, C(13)H or C(14)H), 130.3 (s, 2C, C(18)H), 130.3 (s, 1C, C(3)H), 131.8 (s, 1C, C(11)H), 132.8 (s, 1C, C(2)H), 141.7 (s, 1C, C(1)), 144.5 (s, 1C, C(10)), 146.7 (s, 1C, C(5)), 148.0 ((s, 1C, C(16)), 166.9 (s, 1C, C(9));

Example 7: Synthesis of Reagent 1q

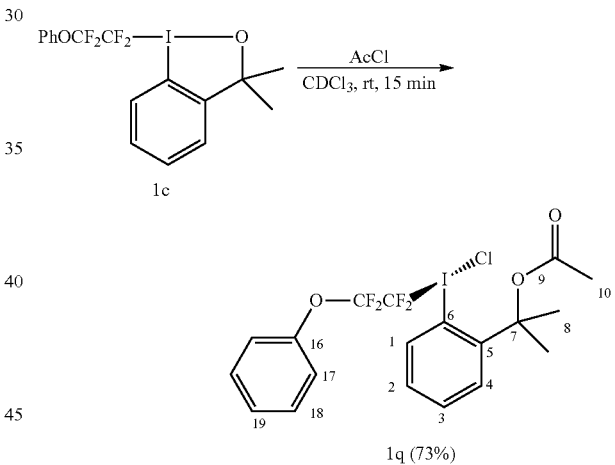

1q (73%)

1c (227 mg, 0.5 mmol) was dissolved in dry CHCl$_3$ (1 ml) under argon atmosphere and acetyl chloride (0.1 ml, 1.5 mmol) was added in one portion. The mixture was stirred 15 minutes at laboratory temperature. After that volatiles were removed under reduced pressure and residue was washed with Et$_2$O to give pure 1q as white particles. Yield: 194 mg (73%); $^1$H NMR (401.00 MHz, CDCl$_3$): δ 2.09 (s, 6H, C(8)H$_3$), 2.22 (s, 3H, C(10)H$_3$), 7.20 (d, $^3J_{HH}$=8.1 Hz, 2H, C(17)H), 7.27-7.37 (m, 2H, C(3)H and C (19)H), 7.42 (t, $^3J_{HH}$=7.8 Hz, 2H, C(18)H), 7.63-7.78 (m, 2H, C(2)H and C(4)H), 8.37 (d, $^3J_{HH}$=8.0 Hz, 1H, C(1)H); $^{19}$F NMR (377.28 MHz, CDCl$_3$): δ -87.8 (s, 2F, CF$_2$I), -84.3 (t, $^3J_{FF}$=6.8 Hz, 2F, CF$_2$O); $^{13}$C {$^1$H} NMR (100.84 MHz, CDCl$_3$): δ 22.9 (s, 1C, C(10)H$_3$), 28.7 (s, 2C, C(8)H$_3$), 82.2 (s, 1C, C(7)), 112.9 (tt, $^1J_{CF}$=345.1 Hz, $^2J_{CF}$=40.7 Hz, 1C, ICF$_2$), 114.4 (s, 1C, C(6)), 116.5 (tt, $^1J_{CF}$=277.2 Hz, $^2J_{CF}$=25.8 Hz, 1C, OCF$_2$), 121.5 (s, 2C, C(17)H), 127.3 (s, 1C, C(19)H), 129.6 (s, 1C, C(4)H), 130.0 (s, 2C, C(18)H), 131.0 (s, 1C, C(3)H), 133.2 (s, 1C, C(2)H), 141.8 (s, 1C, C(1)), 145.6 (s, 1C, C(5)), 148.2 (s, 1C, C(16)), 169.4 (s, 1C, C(9)); HRMS (m/z, ESI⁺): [M+Na]⁺ calc. for $C_{19}H_{18}O_3ClF_4INa$ 554.9818, found, 554.9811.

Example 8: Synthesis of Reagent 1r

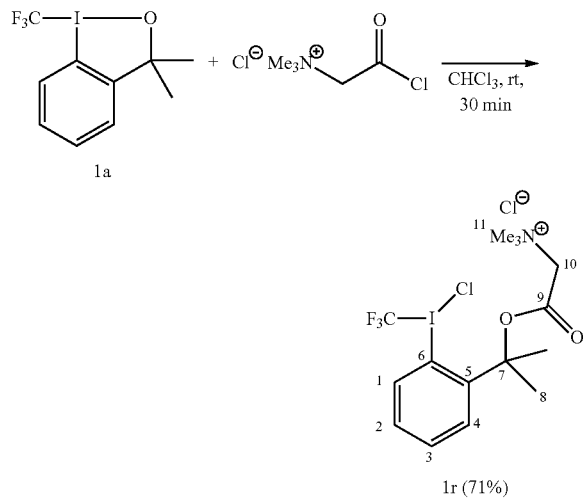

N-2-Chlorocarbonylmethyl-N,N,N-trimethylammonium chloride (56 mg, 0.33 mmol) was suspended in dry CHCl₃ (1 ml) under argon atmosphere and 1a (109 mg, 0.33 mmol) was added in one portion. The suspension was stirred for 30 min under ambient temperature, then diluted with Et₂O (1 ml). White particles were filtered and dried under reduced pressure. Yield: 166 mg (71%, purity 75%, 25% unreacted betaine); ¹H NMR (401.00 MHz, DMSO-d₆): δ 2.00 (bs, 6H, C(8)H₃), 3.37 (bs, 9H, C(11)H₃), 4.63 (bs, 2H, C(10)H₂), 7.43 (t, ³$J_{HH}$=7.6 Hz, 1H, C(3)H), 7.72 (t, ³$J_{HH}$=7.6 Hz, 1H, C(2)H), 7.81 (d, ³$J_{HH}$=8.0 Hz, 1H, C(4)H), 8.51 (d, ³$J_{HH}$=7.8 Hz, 1H, C(1)H); ¹⁹F NMR (377.28 MHz, DMSO-d₆): δ −34.3 (s, 3F, CF₃); ¹³C {¹H} NMR (100.84 MHz, DMSO-d₆): δ 27.3 (s, 2C, C(8)H₃), 53.4 (s, 3C, C(11)H₃), 63.8 (s, 1C, C(10)H₂Cl), 84.4 (s, 1C, C(7)), 108.4 (q, ¹$J_{CF}$=391.5 Hz, 1C, CF₃), 120.7 (s, 1C, C(6)), 128.6 (s, 1C, C(4)H), 131.11 (s, 1C, C(3)H), 132.3 (s, 1C, C(2)H), 141.4 (s, 1C, C(1)), 143.0 (s, 1C, C(5)), 163.5 (s, 1C, C(9)); HRMS (m/z, ESI⁺): [M-Cl]⁺ calc. for $C_{15}H_{21}O_2NClF_3I$ 466.0252, found 466.0248.

Example 9: Synthesis of Reagent 1s

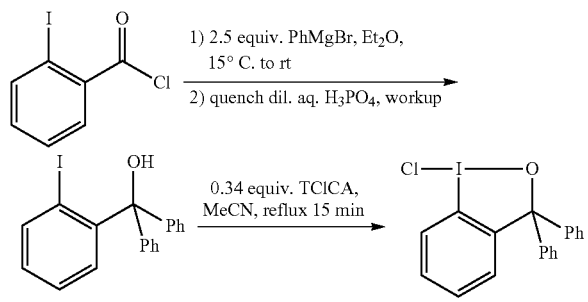

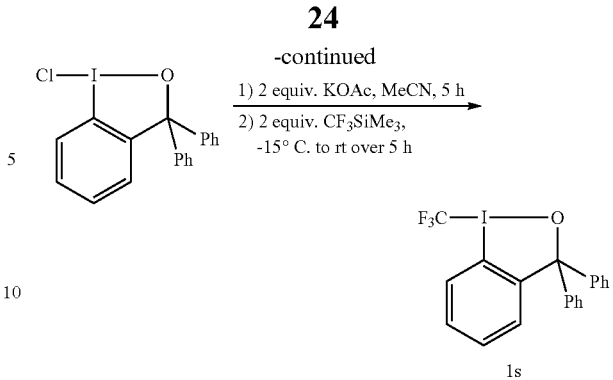

In a 3-necked round-bottom flask equipped with a thermometer and under Ar atmosphere, a solution of phenylmagnesium bromide in diethyl ether (63 ml of 1.49 M solution, 93.8 mmol, 2.5 equiv.) was added followed by addition of further diethyl ether (40 ml). The resulting mixture was cooled in water bath to 15° C. and a solution of 2-iodobenzoylchloride (10 g, 37.5 mmol, 1 equiv.) in diethyl ether (10 ml) was added dropwise so that the internal temperature does not exceed 25° C. After the addition was complete, the reaction mixture was stirred for 3 h at room temperature. Afterwards, the biphasic brown reaction mixture is poured onto well-stirred cold diluted phosphoric acid (150 ml, 20%) until all magnesium salts dissolve. The organic phase was separated, the aqueous phase was extracted with ethyl acetate (2×70 ml). The pooled organic phases were washed with brine and dried over magnesium sulfate and filtered. The filtrate gave upon evaporation and drying on high vac a brown viscous oil in nearly quantitative yield (14.8 g, approx. 90% purity). The crude (2-iodophenyl)diphenylmethanol was taken directly into the next step.

The crude 2-iodophenyl)diphenylmethanol (5 g in 90% purity, 11.6 mmol, 1 equiv.) was dissolved in acetonitrile (40 ml) and heated to 70° C. In a separate flask, trichloroisocyanuric acid "TCICA" (916 mg, 3.94 mmol, 0.34 equiv.) was dissolved in acetonitrile (10 ml). To the well-stirred solution of crude 2-iodophenyl)diphenylmethanol was slowly added the solution of TCICA and the resulting mixture was refluxed for 15 min. The precipitated isocyanuric acid was filtered off, the solution was concentrated to dryness, suspended in a mixture of pentane/diethyl ether (4/1 v/v, 70 ml) and cooled to −15° C. with stirring. The yellowish solid (1-chloro-3,3-diphenyl-1,3-dihydro-1λ3-benzo[d][1,2]iodaoxole) was collected by filtration and washed with little precooled pentane and dried in high vacuum (1.83 g, 37%).

In a Schlenk flask equipped with a magnetic stirring bar, potassium acetate (326 mg, 3.32 mmol, 2 equiv.) was dehydrated with heatgun under vacuum and then backfilled with Ar. To the cooled Schenk was added 1-chloro-3,3-diphenyl-1,3-dihydro-1l3-benzo[d][1,2]iodaoxole (700 mg, 1.66 mmol, 1 equiv.) followed by anhydrous acetonitrile (8 ml) and the resulting mixture was stirred at room temperature for 5 h. Subsequently, the reaction mixture was cooled to −15° C. and trifluoromethyl trimethylsilane (472 mg, 5 mmol, 2 equiv.) was added at once. The reaction mixture was warmed up to room temperature over the course of 5 h, then was filtered over a pad of Celite and concentrated to dryness on rotavap. The brownish oil was redissolved in a mixture of pentane/diethylether (3/1 v/v, 20 ml) and filtered through a pad of alumina. The resulting filtrate was again concentrated to dryness and subjected to silica gel chromatography (gradient elution hexane to hexane/diethylether 1:1) to give after evaporation to dryness is as a yellowish viscous oil. Yield: 196 mg (26%). HRMS (m/z, ESI+): [M+Na]⁺ calc. for $C_{20}H_{14}F_3INaO$, 476.9939, found, 476.9933.

Example 10: Synthesis of Reagent 1t

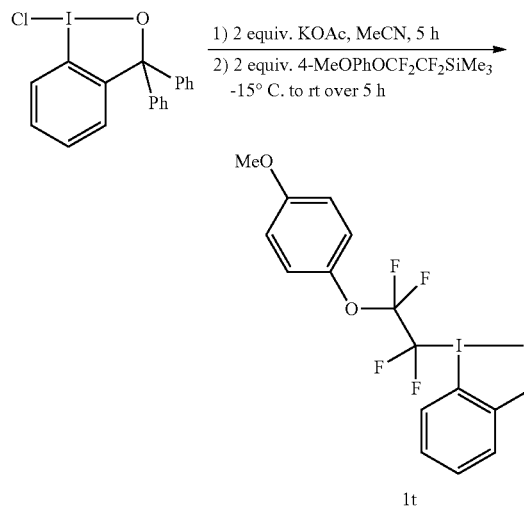

In a Schlenk flask equipped with a magnetic stirring bar, potassium acetate (326 mg, 3.32 mmol, 2 equiv.) was dehydrated with heatgun under vacuum and then backfilled with Ar. To the cooled Schenk was added 1-chloro-3,3-diphenyl-1,3-dihydro-1l3-benzo[d][1,2]iodaoxole (700 mg, 1.66 mmol, 1 equiv.) followed by anhydrous acetonitrile (7 ml) and the resulting mixture was stirred at room temperature for 5 h. Subsequently, the reaction mixture was cooled to −15° C. and a solution of trimethyl(1,1,2,2-tetrafluoro-2-(4-methoxyphenoxy)ethyl)silane (983 mg, 3.32 mmol, 2 equiv.) was added at once. The reaction mixture was warmed up to room temperature over the course of 5 h, then was filtered over a pad of Celite and concentrated to dryness on rotavap. The brownish oil was redissolved in a mixture of pentane/diethylether (3/1 v/v, 20 ml) and filtered through a pad of alumina. The resulting filtrate was again concentrated to dryness and subjected to silica gel chromatography (gradient elution hexane to hexane/diethylether 1:1) to give after evaporation to dryness 1t as a yellow viscous oil. Yield: 192 mg (19%). HRMS (m/z, ESI+): [M+Na]⁺ calc. for $C_{28}H_{21}F_4INaO_3$, 631.0369, found, 631.0377.

Example I: Fluoroalkylation of 3-Methylindole (Scheme 11)

3-Methylindole (66 mg, 0.5 mmol) was dissolved in MeOH (2.14 ml) and the solution was kept under argon atmosphere using the Schlenk line technique. Sodium ascorbate (50 mg, 0.25 mmol, 50 mol %) was dissolved in water (0.72 ml) and added to the solution of substrate in MeOH. 1d (264 mg, 0.6 mmol, 1.2 equiv.) was dissolved in MeOH (2.14 ml) and the resulting solution was slowly (in 5 minutes) added to the mixture of substrate and sodium ascorbate. The reaction mixture was stirred for 5 minutes at room temperature. After this period, the solvent was evaporated and the mixture was partitioned between DCM (30 ml) and water (30 ml). The organic phase was washed with water (3×15 ml), brine (3×15 ml), saturated aq. NaHCO₃ solution (3×15 ml) and dried over MgSO₄, followed by solvent removal under reduced pressure. Purification by flash chromatography (cyclohexane/DCM, 3:1] afforded pure product as a pale yellow oil. Yield: 140 mg (87%); $R_f$=0.27 (cyclohexane/DCM, 3:1); ¹H NMR (400 MHz, CD₃OD): δ 2.45-2.47 (t, J=2.2 3H, CH₃), 7.07-7.14 (m, 3H, $C_{Ar}$ H), 7.20-7.26 (m, 2H, $C_{Ar}$ H), 7.31-7.38 (m, 2H, $C_{Ar}$ H), 7.41-7.44 (m, 1H, $C_{Ar}$ H), 7.59-7.62 (m, 1H, $C_{Ar}$H); ¹⁹F NMR (376 MHz, CD₃OD): δ −86.46 to −86.50 (t, ³$J_{FF}$=6.4, 2F, CF₂), δ −110.81 to −110.86 (tt, ³$J_{FF}$=6, 2F, CF₂); ¹³C {¹H, ¹⁹F} NMR (126 MHz, CD₃OD): δ 9.20 (3H, CH₃), 113.02, 115.05, 115.38, 119.75, 120.68, 120.79, 122.88, 123, 125.09, 127.91, 129.76, 131.11, 138.05, 150.82; HRMS (ESI) m/z Calcd for $C_{17}H_{13}F_4NO$ [M]⁺ 323.0933, found 323.0932.

Example II: Fluoroalkylation of a Protected Tryptophan Derivative

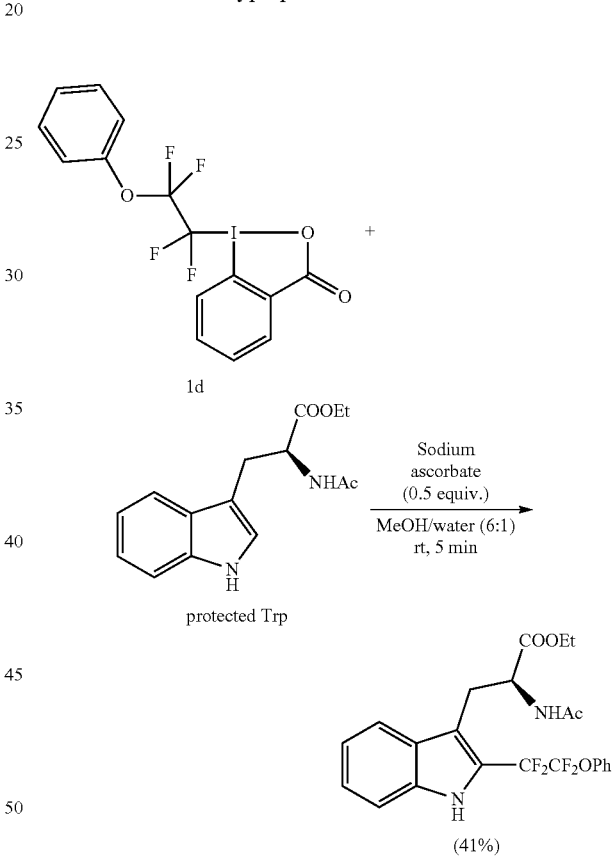

Protected Trp derivative (137 mg, 0.5 mmol) was dissolved in MeOH (1.1 ml) and the solution was kept under argon atmosphere using the Schlenk line technique. Sodium ascorbate (50 mg, 0.25 mmol, 50 mol %) was dissolved in water (0.7 ml) and added to the solution of substrate in MeOH. 1cl (264 mg, 0.6 mmol, 1.2 equiv.) was dissolved in MeOH (1 ml) and the resulting solution was slowly (in 5 minutes) added to the mixture of substrate and sodium ascorbate. The reaction mixture was stirred for 5 minutes at room temperature. After this period, the solvent was evaporated and the mixture was partitioned between DCM (30 ml) and water (30 ml). The organic phase was washed with water (3×15 ml), brine (3×15 ml), saturated aq. NaHCO₃ solution (3×15 ml) and dried over MgSO₄, followed by solvent removal under reduced pressure. Purification by flash chromatography (cyclohexane/DCM, 6:1] afforded pure product as a pale brown oil. Yield: 95 mg (41%); $R_f$=0.3 (cyclohexane/DCM, 6:1); $^1$H NMR (400 MHz, CD$_3$OD): δ 0.95-0.99 (t, J=7.1, 3H), 1.22-1.26 (t, J=7.1, 1H), 1.92 (s, 2H), 2.01 (s, 1H), 3.34-3.51 (m, 2H), 4.74-4.78 (m, 1H), 7.13-7.18 (m, $C_{Ar}$H, 3H), 7.24-7.29 (m, $C_{Ar}$H, 2H), 7.34-7.39 (m, $C_{Ar}$H, 2H), 7.45-7.48 (m, $C_{Ar}$H, 1H), 7.69-7.71 (m, $C_{Ar}$H, 1H); HRMS (ESI) m/z Calcd for $C_{23}H_{22}F_4N_2O_4$ [M–H]$^+$ 466.15, found 466.1520.

Example III: Fluoroalkylation of Amino Acids

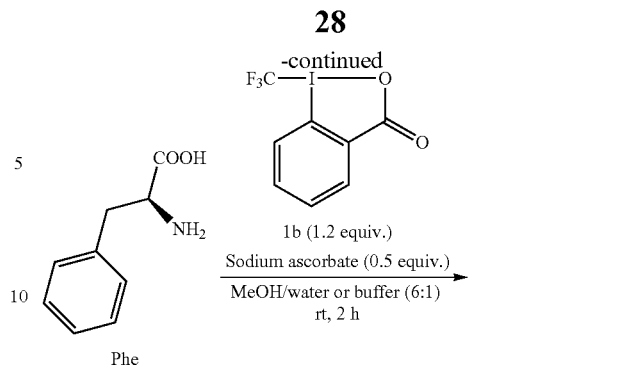

Experiment IIIa—Trifluoromethylation of Individual Aromatic Amino Acids

To a solution of amino acid (0.1 mmol) in MeOH (0.2 ml) was added a solution of reagent 1b (0.12 mmol, 1.2 equiv.) in MeOH (0.65 ml). A solution of sodium ascorbate (0.05 mmol) in water or buffer of pH 5 (phosphate) or pH 9 (carbonate/acetate) (0.15 ml) was added dropwise over 2 minutes. After 2 h of stirring at 25° C. the resulting mixture was analyzed by $^{19}$F NMR to determine NMR yield using sodium trifluoroacetate as an internal standard (Table 1).

TABLE 1

$^{19}$F NMR yields of fluoroalkylation of amino acids with 1b

| Aminoacid | pH | Product yield (%) |
|---|---|---|
| Trp | — | 76 |
| Tyr | — | 9 |
|  | 9 | 20 |
| Phe | 5 | 0 |
|  | 9 | 2 |

TABLE 1-continued

| $^{19}$F NMR yields of fluoroalkylation of amino acids with 1b | | |
|---|---|---|
| Aminoacid | pH | Product yield (%) |
| His | — | 5 |
| | 5 | 2 |
| | 9 | 13 |

Figure 2:
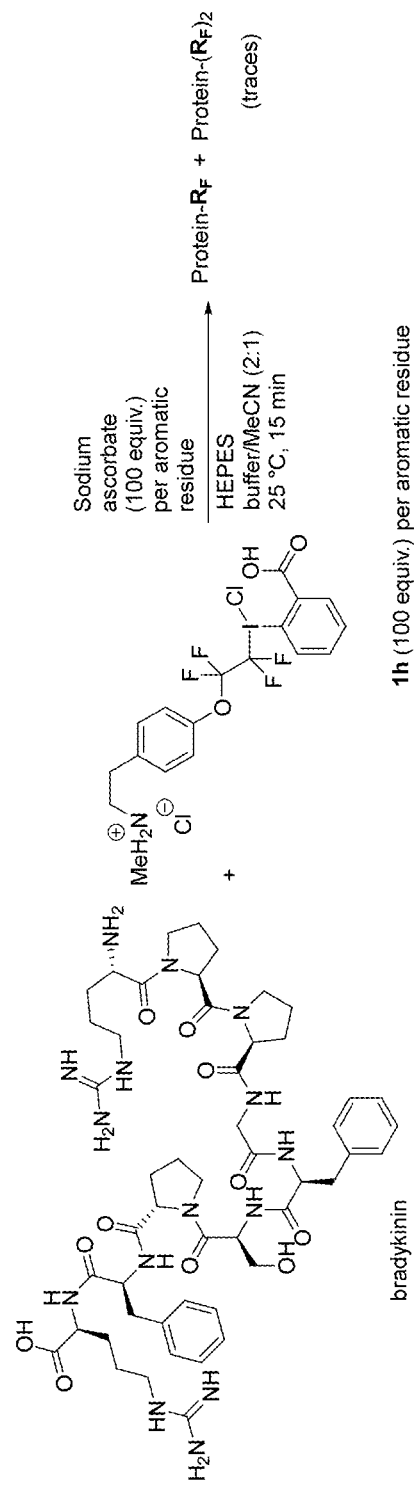
FIG. 2: Fluoroalkylation of peptide bradykinin

In a separate experiment, stock solutions of natural amino acid standards (Trp, Tyr, Phe, His, Gly, Ala, Ser, Pro, Val, Thr, Ile, Leu, Asn, Asp, Glu, Gln, Arg, Lys, Met (Waters, 5 mM standard solution at pH=7.5) were dissolved in an ammonium bicarbonate buffer (pH=7.5, 50 mM) to reach the final concentration 2 mM for each amino acid. Reagent 1a (10 equiv. calculated to each amino acid, 30 mM solution in DMSO) was added followed by ascorbic acid (5 equiv. calculated to each amino acid, 283 mM solution in water) were added. After stirring at 25° C. for 15 minutes, semi-quantitative LCMS analysis shower reactivity order as follows: Trp>>Tyr>Phe>His. Extracted-ion chromatograms indicated that only aromatic aminoacids and cystine underwent fluoroalkylation (FIG. 2).

| Amino Acid | Trifluoro-methylation detected? | m/z | Note |
|---|---|---|---|
| Trp | Yes | 273.085 (monofluoro-alkylation) | 1 major isomer along with 2 minor isomers detected |
| Trp | Yes | 341.072 (bis(fluoro-alkylation)) | 2 isomers detected |
| Tyr | Yes | 250.069 (monofluoro-alkylation) | 1 major isomer detected |
| Phe | Yes | 234.074 | 2 isomers detected |
| His | Yes | 224.064 | 1 major isomer detected |
| Gly, Ala, Ser, Pro, Val, Thr, Leu, Ile, Asn, Asp, Gln, Lys, Glu, Met, Arg | No | N/A | No mass corresponding to trifluoromethylated amino acids could be detected |

Example IV: Fluoroalkylation of Peptide AFRIPLYWGRI (FIG. 1)

A solution of peptide AFRIPLYWGRI (1 mg) in MeCN (0.7 ml) containing 1% formic acid and water (0.3 ml) was prepared. Solution of 1d (50 mM) in MeCN and a solution of sodium ascorbate (50 mM) in water were prepared. Solution of the peptide (45 µl) was diluted with water (0.4 ml) containing methionine (20 mM) and to 0.1 ml of this solution 1.46 µl of ascorbate solution was added. Finally, the solution of hypervalent iodine reagent (1.46 µl, 10 equiv.) was added and the mixture was vortexed for a few seconds. After 1 h at ambient temperature the mixture was analyzed by MALDI MS: m/z starting peptide calcd for $C_{69}H_{104}N_{19}O_{12}$ [M+H]$^+$ 1390.8112, found 1390.8065; peptide+one modification calcd for $C_{77}H_{108}F_4N_{19}O_{13}$ [M+H]$^+$ 1582.8310, found 1582.8227; peptide+two modifications calcd for $C_{84}CH_{112}F_8N_{19}O_{14}$ [M+H]$^+$ 1775.8542, found 1775.8403. MS/MS analysis confirmed that monofluoroalkylation took place only on Trp.

| AFRIPLYWGRI m/z | Reagent | AFRIPLYWGRI approx. conversion | Masses detected |
|---|---|---|---|
| 1390.8065 | 1d | High | 1582.8227 (monofluoroalkylated) 1775.8403 (bis(fluoroalkylated)) |

Example V: Fluoroalkylation of Peptide Bradykinin (FIG. 2)

Bradykinin (1 equiv. as 1 mg/ml degassed solution in 20% v/v MeCN/50 mM pH 7 HEPES buffer) was mixed with sodium ascorbate (100 equiv. calculated to molar amount of aromatic residues, 20 mM solution in water) and solution of 1h was added (100 equiv. calculated to molar amount of aromatic resides, 8.7 mM in 50% v/v MeCN/H$_2$O) The mixture was shaken for 15 min at 25° C. MALDI MS analysis indicated partial formation of fluoroalkylated bradykinin and traces of 2× fluoroalkylated bradykinin MS/MS analysis revealed that Phe residue is fluoroalkylated.

| Bradykinin m/z | Reagent | Bradykinin approx. conversion | Masses detected |
|---|---|---|---|
| 1060.626 | 1h | Low | 1309.709 (monofluoroalkylated) 1559.802 (bis(fluoroalkylated)), trace |

Figure 3:
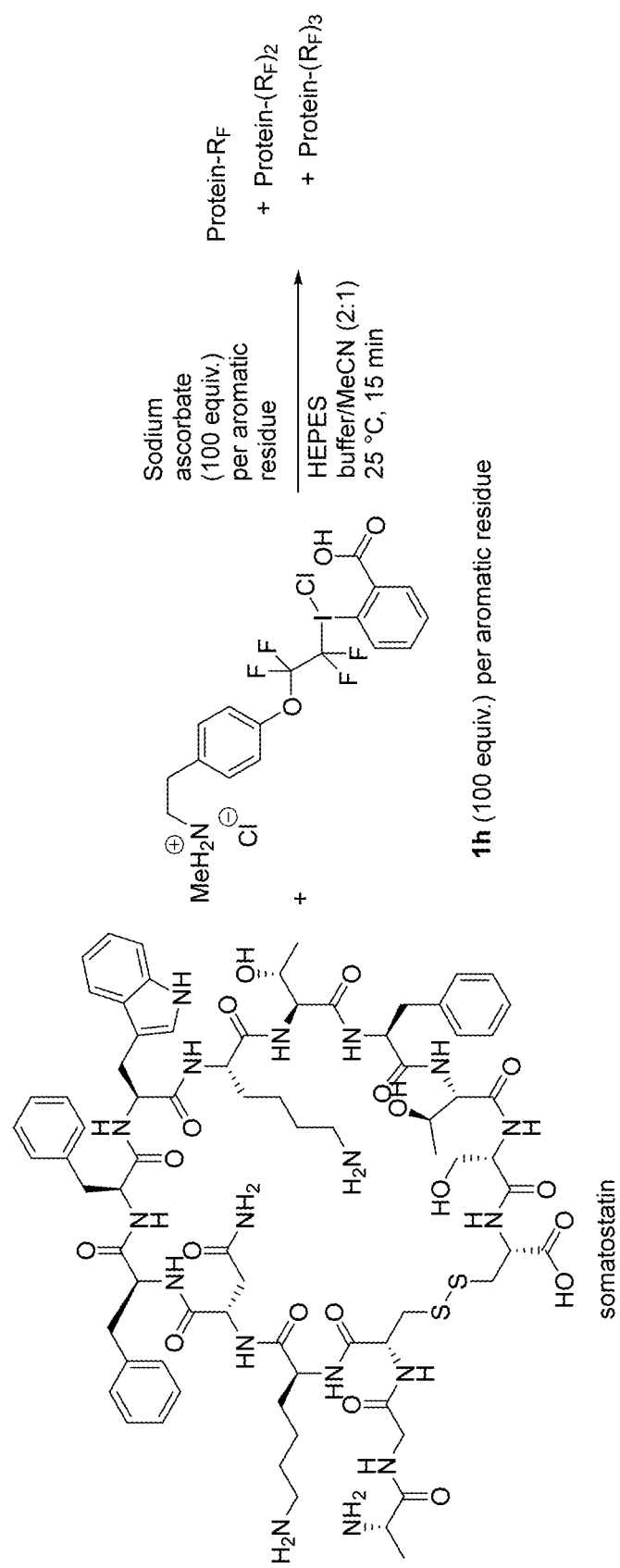
FIG. 3: Fluoroalkylation of peptide somatostatin

Example VI: Fluoroalkylation of Peptide Somatostatin (FIG. 3)

Somatostatin (1 equiv. as 1 mg/ml degassed solution in 20% v/v MeCN/50 mM pH 7 HEPES buffer) was mixed with sodium ascorbate (100 equiv. calculated to molar amount of aromatic residues, 20 mM solution in water) and solution of 1h was added (100 equiv. calculated to molar amount of aromatic resides, 8.7 mM in 50% v/v MeCN/H$_2$O). The mixture was shaken for 15 min at 25° C. MALDI MS analysis indicated formation of monofluoroalkylated somatostatin, bis(fluoroalkylated) somatostatin, tris(fluoroalkylated) somatostatin and traces of fluoroalkylated oxidized somatostatin. MS/MS analysis revealed that the only positions of first and second modification were on the Trp residue.

| Somatostatin m/z | Reagent | Somatostatin conversion | Masses detected |
|---|---|---|---|
| 1637.819 | 1h | High | 1886.897 (monofluoroalkylated) 2135.979 (bis(fluoroalkylated)) 2385.073 (tris(fluoroalkylated), trace) |

Figure 4:
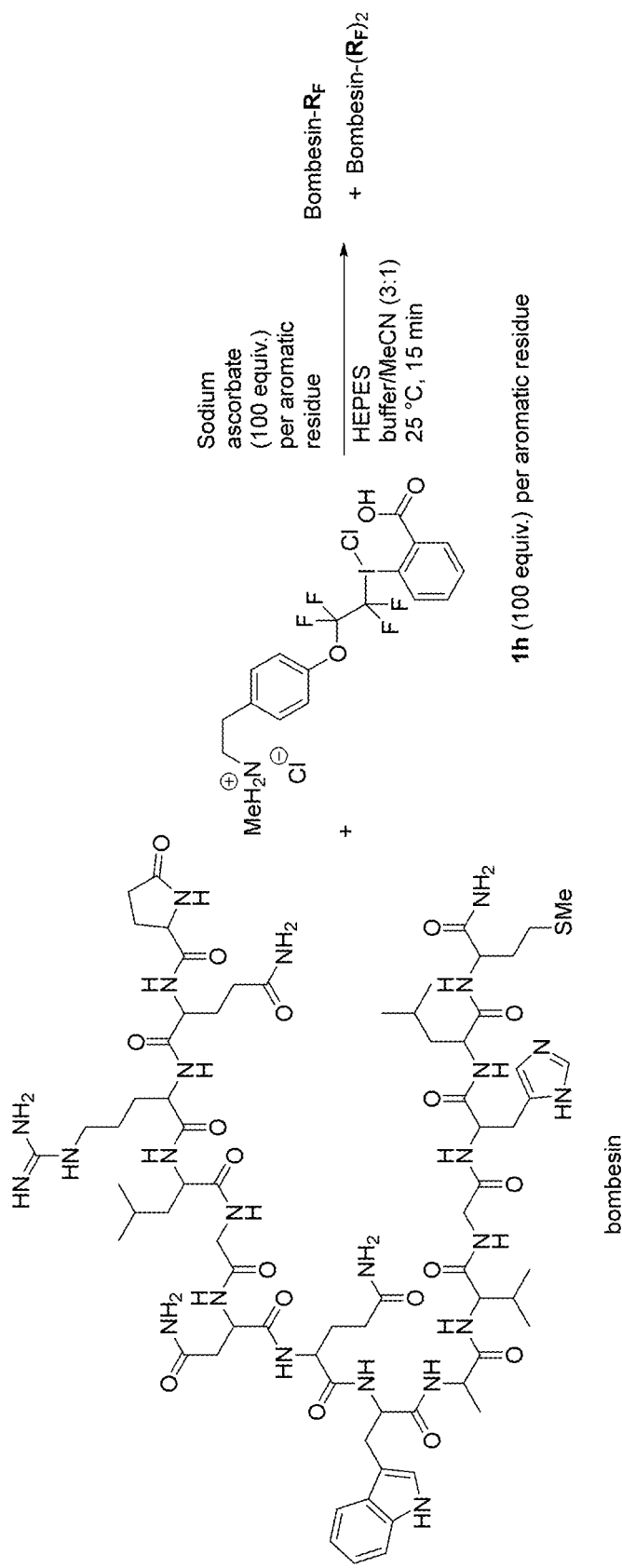
FIG. 4: Fluoroalkylation of peptide bombesin

Example VII: Fluoroalkylation of Peptide Bombesin (FIG. 4)

Bombesin (1 equiv. as 1 mg/ml degassed solution in 20% v/v MeCN/50 mM pH 7 HEPES buffer) was mixed with sodium ascorbate (100 equiv. calculated to molar amount of aromatic residues, 20 mM solution in water) and solution of 1h was added (100 equiv. calculated to molar amount of aromatic resides, 8.7 mM in 50% v/v MeCN/H₂O). The mixture was shaken for 15 min at 25° C. MALDI MS analysis indicated formation of monofluoroalkylated bombesin, bis(fluoroalkylated) bombesin and traces of tris(fluoroalkylated) bombesin and oxidized fluoroalkylated bombesin. MS/MS analysis revealed that the only positions of first and second modification were on the Trp residue.

| Bombesin m/z | Reagent | Bombesin approx. conversion | Masses detected |
|---|---|---|---|
| 1619.944 | 1h | High | 1868.974 (monofluoroalkylated) |
| | | | 1884.967 (monofluoroalkylated, monooxidized, trace) |
| | | | 2118.047 (bis(fluoroalkylated)) |
| | | | 2134.038 (bis(fluoroalkylated), monooxidized, trace) |
| | | | 2369.139 (tris(fluoroalkylated), trace) |

Example VIII: Fluoroalkylation of Insulin

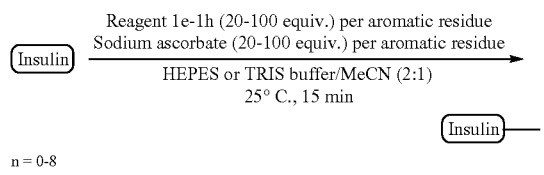

$n = 0-8$

Human recombinant insulin in HEPES or TRIS buffer (pH 7-9) was subjected to fluoroalkylation with reagents 1e-1h (20-100 equiv. calculated to molar amount of aromatic residues) in MeCN and sodium ascorbate (20-100 equiv. calculated to molar amount of aromatic residues) at 25° C. for 15 min. The comparison of reagents 1e and 1f revealed that the "acid-type" reagent 1f gave a deeper degree of fluoroalkylation (up to 8 modifications). To determine the site of fluoroalkylation after the reaction, the A and B chains of insulin were reductively cleaved by the treatment with DTT and the individual chains were subjected to MS/MS analysis. MS/MS analysis showed (experiment with reagents 1f at pH 8) that Phe and Tyr residues were fluoroalkylated at roughly equal proportions, while there was a minor fluoroalkylation of histidine.

Another experiments were carried out using 100 equiv. of reagents 1g or 1h (calculated to molar amount of aromatic residues), 100 equiv. of sodium ascorbate (calculated to molar amount of aromatic residues) at pH 7, 8 and 9. It was found that at pH 9 the extent of fluoroalkylation was higher than in pH 7 and 8.

| Human recombinant insulin m/z | Reagent, note | Insulin approx. conversion | Masses detected |
|---|---|---|---|
| 5809 | 1e 20 equiv ascorbate, 100 equiv 1e used | Medium | 5975 (monofluoroalkylated) |
| | | | 6141 (bis(fluoroalkylated)) |
| | | | 6307 (tris(fluoroalkylated)) |
| | | | 6474 (tetrakis(fluoroalkylated), trace) |
| | | | 6641 (pentakis(fluoroalkylated), trace) |
| | | | 6810 (hexakis(fluoroalkylated), trace) |
| 5809 | 1f 20 equiv ascorbate, 100 equiv 1f used | High | 5975 (monofluoroalkylated) |
| | | | 6142 (bis(fluoroalkylated)) |
| | | | 6308 (tris(fluoroalkylated)) |
| | | | 6475 (tetrakis(fluoroalkylated), trace) |
| | | | 6641 (pentakis(fluoroalkylated), trace) |
| | | | 6807 (hexakis(fluoroalkylated), trace) |
| | | | 6973 (heptakis(fluoroalkylated), trace) |
| | | | 7139 (octakis(fluoroalkylated), trace) |

| Human recombinant insulin m/z | Reagent | pH and buffer | Approx. conversion | Masses detected |
|---|---|---|---|---|
| 5809 | 1g | pH = 7, HEPES buffer | 21% | 6057 (monofluoroalkylated) 6308 (bis(fluoroalkylated)) |
| 5809 | 1g | pH = 8, HEPES buffer | 20% | 6057 (monofluoroalkylated) 6308 (bis(fluoroalkylated)) |
| 5809 | 1g | pH = 9, TRIS buffer | 63% | 6057 (monofluoroalkylated) 6308 (bis(fluoroalkylated)) |
| 5809 | 1h | pH = 7, HEPES buffer | 24% | 6057 (monofluoroalkylated) 6308 (bis(fluoroalkylated)) |
| 5809 | 1h | pH = 8, HEPES buffer | 25% | 6057 (monofluoroalkylated) 6308 (bis(fluoroalkylated)) |
| 5809 | 1h | pH = 9, TRIS buffer | 71% | 6057 (monofluoroalkylated) 6308 (bis(fluoroalkylated)) |

Example IX: Fluoroalkylation of Ubiquitin—Protein Modification

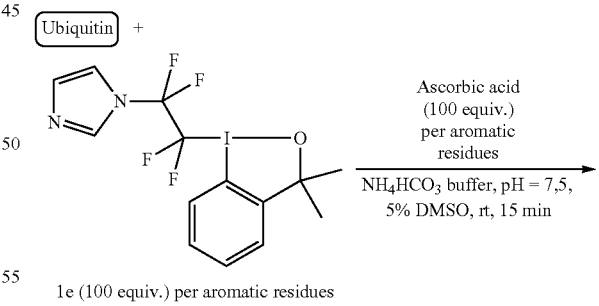

1e (100 equiv.) per aromatic residues

A stock solution of ubiquitin from bovine erythrocytes in water was diluted in 50 mM ammonium bicarbonate buffer (pH 7.5) to reach 58 μM concentrations (0.5 mg/ml). Freshly prepared solution of ascorbic acid in water (283 mM, 100 equiv. calculated to molar amount of aromatic residues) and 1e in DMSO (10 mg/1 ml, 100 equiv. calculated to molar amount of aromatic residues) were added and the reaction mixture which was incubated for 15 min at 25° C. The mixture was desalted using Peptide Microtrac in the off-line holder (MichromBioresources) according manufacturer instruction, and eluted with 50 µl of 80% MeCN/5% AcOH. The protein was analysed using solariX XR FT-ICR mass spectrometer (Bruker Daltonics) equipped with a 15T superconducting magnet and ParaCell. The instrument was internally calibrated using Agilent tuning mix (Agilent Technologies, USA). Mass spectra were acquired in the positive mode over the m/z range 250-2500 with 2 M data points transient and 1 s ion accumulation, 8 scans were accumulated per spectrum. Data acquisition and data processing were performed using ftmsControl 2.2.0 and DataAnalysis 5.0. ESI MS spectra revealed predominantly monofluoroalkylation of the protein.

| Ubiquitin m/z | Reaction conditions | Approximate conversion | Masses detected |
|---|---|---|---|
| 779.15658 (11+ charge state) | 10 equiv. 1e, 10 equiv. ascorbate | Negligible | — |
| 779.15658 (11+ charge state) | 100 equiv. 1e, 100 equiv. ascorbate | Medium | 794.24967 (monofluoroalkylated, 11+ charge state) 809.34281 (bis(fluoroalkylated), 11+ charge state, trace) |
| 714.30842 (12+ charge state) | 1k | Medium | 728.39401 (monofluoroalkylated, 12+ charge state) 794.52022 (monofluoroalkylated, 11+ charge state) |
| 714.30842 (12+ charge state) | 1k, followed by incubation with DBCO-amine | Medium | 751.40587 (monofluoroalkylated and ligated with DBCO-amine, 12+ charge state) 819.62388 (monofluoroalkylated, 11+ charge state) |

Example X: Fluoroalkylation of Ubiquitin Followed by Click Reaction of the Conjugate

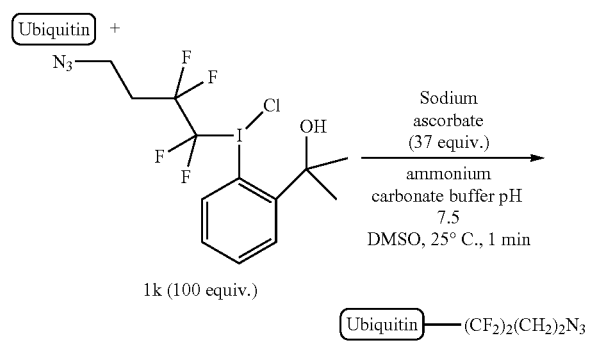

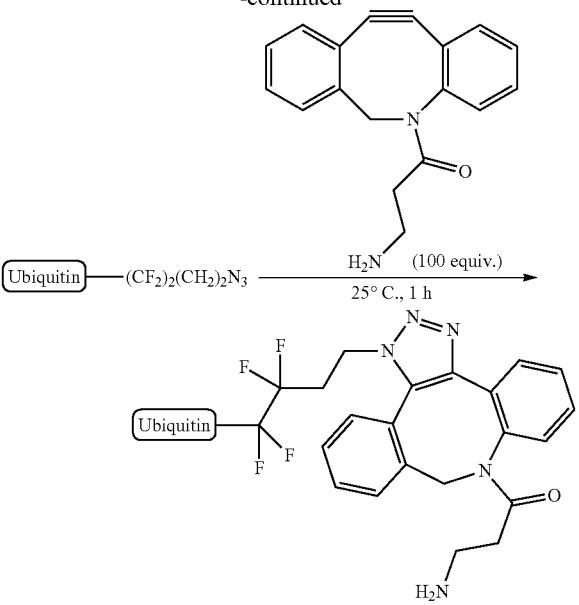

A stock solution of ubiquitin from bovine erythrocytes in water was transferred to 50 mM ammonium bicarbonate buffer (pH 7.5) using a micro BioSpin 6 column (Biorad) and diluted in same buffer to reach 58 µM concentrations (0.5 mg/ml). Freshly prepared solution of ascorbic acid in water (50 mg/ml, 37 equiv.) and 1k in DMSO (10 mg/1 ml, 100 equiv.) were added and the reaction mixture was incubated for 1 min at 25° C. and transferred to 50 mM ammonium bicarbonate buffer pH 7.5 using a micro BioSpin 6 column in order to eliminate the effect of side products of radical reaction or unreacted ascorbic acid. In the second step, the fluoroalkylated ubiquitin solution was mixed with DBCO-amine (100 equiv.) and incubated for 1 hour at 25° C. in the dark. The mixture was desalted using Peptide Microtrap in the off-line holder (MichromBioresources) according to manufacturer's instructions, and eluted with 50 µl of 80% MeCN/5% AcOH. The protein was analysed using solariX XR FT-ICR mass spectrometer (Bruker Daltonics) equipped with a 15T superconducting magnet and ParaCell. The instrument was internally calibrated using Agilent tuning mix (Agilent Technologies, USA). Mass spectra were acquired in the positive mode over the m/z range 250-2500 with 2 M data points transient and 1 s ion accumulation, 8 scans were accumulated per spectrum. Data acquisition and data processing were performed using ftmsControl 2.2.0 and DataAnalysis 5.0. ESI-MS indicated that ubiquitin underwent predominantly monofluoroalkylation with trace bis(fluoroalkylation) and the mono- and bis(fluoroalkylated) ubiquitin subsequently underwent clean copper-free click reaction with a dibenzocyclooctyne-amine reagent, affording the corresponding desired conjugates.

| Ubiquitin m/z | Reaction conditions | Approximate conversion | Masses detected |
|---|---|---|---|
| 714.30842 (12+ charge state) | 1k | Medium | 728.39401 (monofluoroalkylated, 12+ charge state) 794.52022 (monofluoroalkylated, 11+ charge state) |

-continued

| Ubiquitin m/z | Reaction conditions | Approximate conversion | Masses detected |
|---|---|---|---|
| 714.30842 (12+ charge state) | 1k, followed by incubation with DBCO-amine | Medium | 751.40587 (monofluoroalkylated and ligated with DBCO-amine, 12+ charge state) 819.62388 (monofluoroalkylated, 11+ charge state) |

Example XI: Human Carbonic Anhydrase I—Aminoacid Side Chains Reactivity on Protein For the reaction, a stock solution of carbonic anhydrase I from bovine erythrocytes (hCA I, Merck) in water was transferred to 50 mM ammonium bicarbonate buffer pH 7.5 using a micro BioSpin 6 column (Biorad) and diluted in same buffer to reach 17 µM concentration (0.5 mg/me. Freshly prepared solution of ascorbic acid in water and one of reagents (1a, 1b, 1e and 1f) in DMSO were added in 150× and 200× molar excess to protein, respectively. The reaction mixture was incubated 10 min at room temperature and mixed with 4× concentrated LDS sample buffer (Invitrogen) containing 100 mM dithiothreitol as the reducing agent in a 3:1 (v/v) ratio. Samples were loaded onto a NuPage 4-12% Bis-Tris gel (80.0×80.0×1.0 mm, 10 wells, Invitrogen). Separation was performed in MES running buffer (Invitrogen) for 35 min at 200 V. After separation, the gels were stained by Coomassie Brilliant Blue R250 and destained with ethanol, water, and acetic acid in the ratio 55:35:10. Identification of modified hCA I was performed as described previously (Rozbeský, D.; Rosůlek, M.; Kukačka, Z.; Chmelík, J.; Man, P.; Novák, P. *Analytical Chemistry* 2018, 90 (2), 1104-1113.) Briefly, bands of the modified enzymes were excised. In gel proteolysis by trypsin was carried out for 6 hours at 37° C. (enzyme:protein ratio 1:20 w/w), dried using SpeedVac and re-suspended in water containing 2% MeCN and 0.1% TFA.

Figure 5:
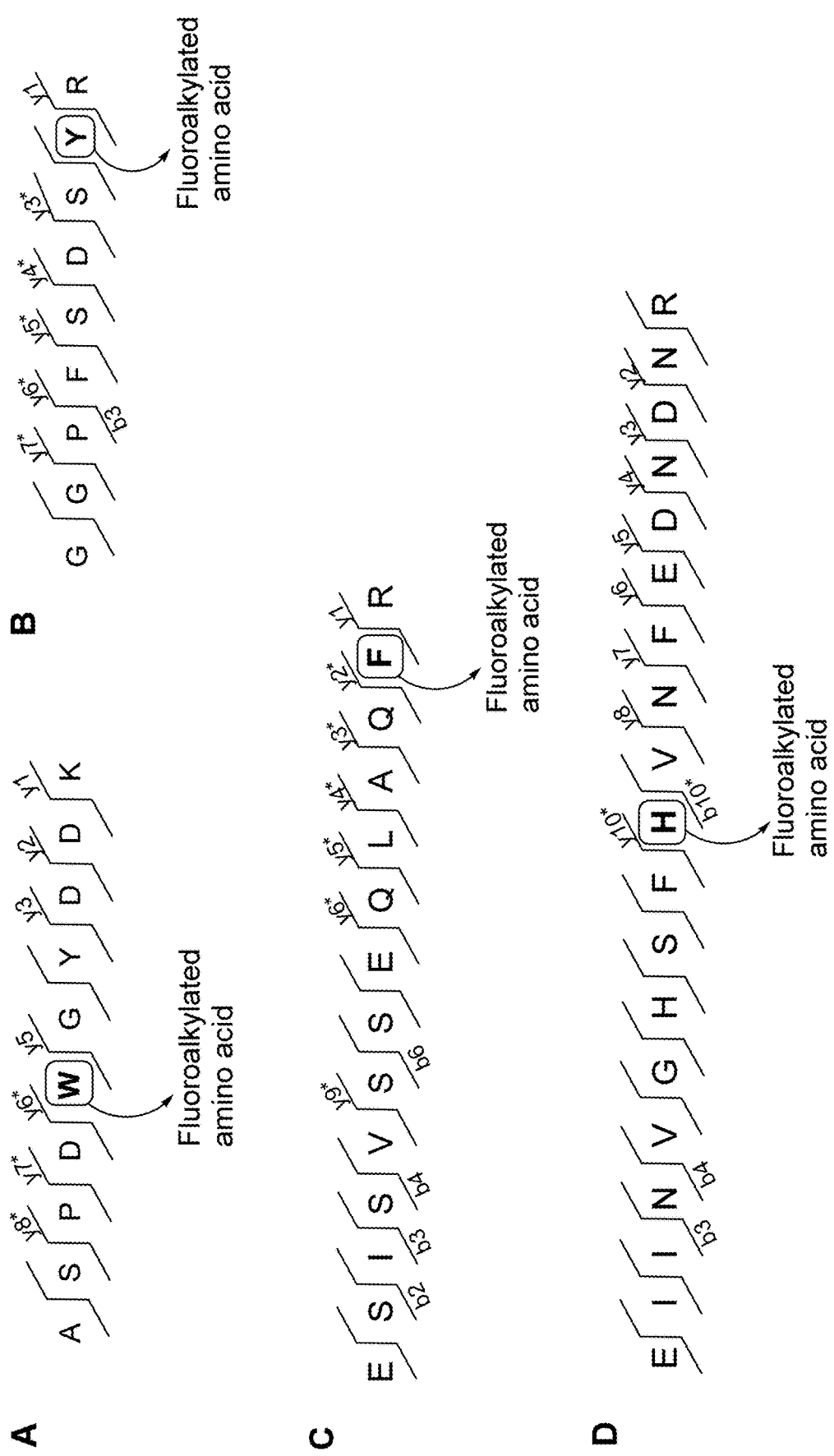
FIG. 5: Identification of hCA I tryptic peptide modified by $CF_3$ radicals using reagent 1a. Based on the fragment spectra tryptophane (A), tyrosine (B), phenylalanine (C) and histidine (D) were determined as residues susceptible to radical fluoroalkylation.
Figure 6:
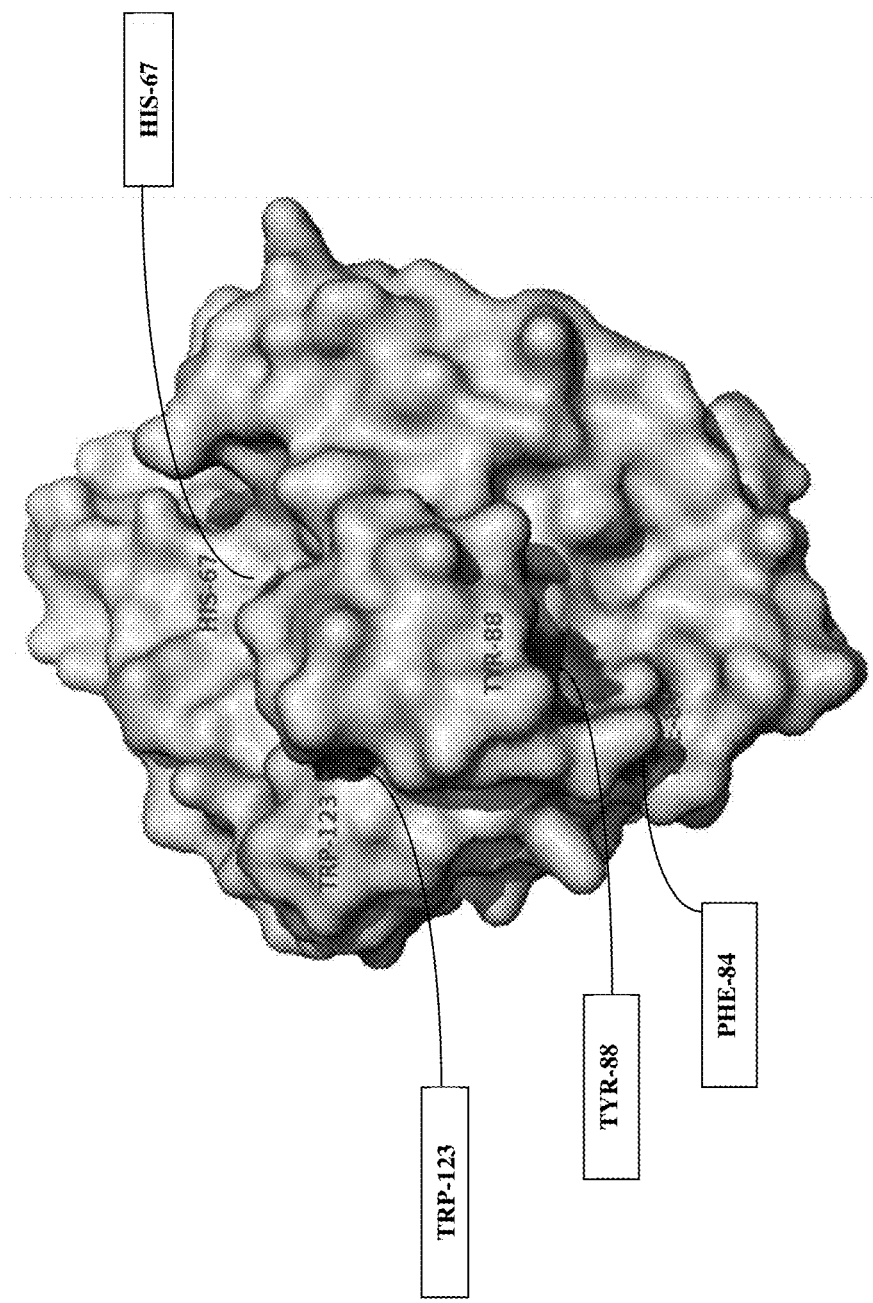
FIG. 6: Red spots represent Trp123, Tyr88, Phe84 and His67 residues on the surface accessible area of hCA I structural model (1hcb).

Nano Reversed phase column (EASY-Spray column, 50 cm×75 µm ID, PepMap C18, 2 µm particles, 100 Å pore size) was used for LC/MS analysis. Mobile phase buffer A was composed of water and 0.1% formic acid. Mobile phase B was composed of acetonitrile and 0.1% formic acid. 1 µg of re-suspended samples were loaded onto the trap column (Acclaim PepMap300, C18, 5 µm, 300 Å Wide Pore, 300 µm×5 mm) at a flow rate of 15 µl/min. Loading buffer was composed of water, 2% MeCN and 0.1% TFA. Peptides were eluted with gradient of B from 4% to 35% over 60 min at a flow rate of 300 nl/min. Eluting peptide cations were converted to gas-phase ions by electrospray ionization and analyzed on a Thermo Orbitrap Fusion (Q-OT-qIT, Thermo). Survey scans of peptide precursors from 350 to 1400 m/z were performed at 120 K resolution (at 200 m/z) with a $5 \times 10^5$ ion count target. Tandem MS was performed by isolation at 1.5 Th with the quadrupole, HCD fragmentation with normalized collision energy of 30, and rapid scan MS analysis in the ion trap. The MS2 ion count target was set to $10^4$ and the max injection time was 35 ms. Only those precursors with charge state 2-6 were selected for MS2. The dynamic exclusion duration was set to 45 s with a 10 ppm tolerance around the selected precursor and its isotopes. Monoisotopic precursor selection was turned on. The instrument was run in top speed mode with 2 s cycles. The data were exported to mgf files and MASCOT 2.0 search engine was used to interpret the data. The precursor mass error was set to 5 ppm, the fragment tolerance was set to 10 ppm, oxidation of methionine (+15.9959 a.m.u), and modification of aromatic residues (66.9784 a.m.u. for 1a,b and 166.0174 a.m.u. for 1e,f) were included as well. Only assignments passing the 1% FDR were considered as positive hits. Such comprehensive analysis revealed thryptophane, tyrosine, phenylalanine and histidine modified by fluoroalkyl radicals in all cases (FIG. 5). The assignment showing the selectivity of fluoroalkyl radical reaction is shown for 1a. According to the MS/MS analysis the Trp123, Tyr88, Phe84 and His67 residues were modified with one $CF_3$ group. All modified residues are solvent accessible using 1hcb structural model of hCA I (FIG. 6), which clearly demonstrated that after radical fluoroalkylation the native structure of the protein was not perturbed.

Example XII: Labelling of Single Stranded DNA (TOP17)-TAATACGACTCACTATA

Single stranded DNA (from IDT company) was dissolved in 50 mM ammonium bicarbonate buffer pH 7.5 to reach 50 µM concentration. Freshly prepared solution of ascorbic acid in water (50 mg/ml) and 1f in DMSO (10 mg/l ml) were added each in 100× molar excess relative to ssDNA. The reaction mixture was incubated for 5 min at room temperature. The labeling reaction was quenched by adding AcOH to 1% final concentration. The reaction products were analyzed using solariX XR FT-ICR mass spectrometer (Bruker Daltonics) equipped with a 15T superconducting magnet and ParaCell. The instrument was internally calibrated using Agilent tuning mix (Agilent Technologies, USA). Mass spectra were acquired in the negative ion mode over the m/z range 200-3000 with 2 M data points transient and 0.5 s ion accumulation, 8 scans were accumulated per spectrum. MS/MS spectra were acquired in for −4 charge state with 2 M data points transient and 2.5 s ion accumulation, 64 scans were accumulated per spectrum. Data acquisition and data processing were performed using ftmsControl 2.2.0 and DataAnalysis 5.0, respectively. The modified ssDNA was identified using MS2links software (cit Kellersberger K A, Yu E, Kruppa G H, Young M M, Fabris D. *Anal Chem.* 2004 May 1; 76(9):2438-45.)

| Oligonucleotide m/z | Reagent | Approximate conversion | Masses detected |
|---|---|---|---|
| 1711.313 (3− charge state) | 1f | Low | 2649.387 (monofluoroalkylated, 2− charge state) 1765.946 (monofluoroalkylated, 3− charge state) 1324.214 (monofluoroalkylated, 4− charge state) |

CID of monofluoroalkylated product ion, 4− charge state (1324.214 m/z)

List of detected ions [w2]⁻ (634.101); [a3-B]⁻ (714.126); [w6]²⁻ (926.143); [w6 + $R_f$]²⁻ (1009.149); [w4]⁻ (1251.191); [a5-B]⁻ (1331.214); [w10]²⁻ (1523.723); [w5]⁻ (1540.253); [w10 + $R_f$]²⁻ (1606.753); [a7-B]⁻ (1933.331); [a12-B]²⁻ (1728.287); [w5 + $R_f$]⁻ (1706.269); [AATAC]⁻ (1725.252); [w6]⁻ (1853.272); [w12]²⁻ (1832.794); [w12 + $R_f$]²⁻ (1925.804); [AATAC + $R_f$]⁻ (1891.268)

Figure 7:
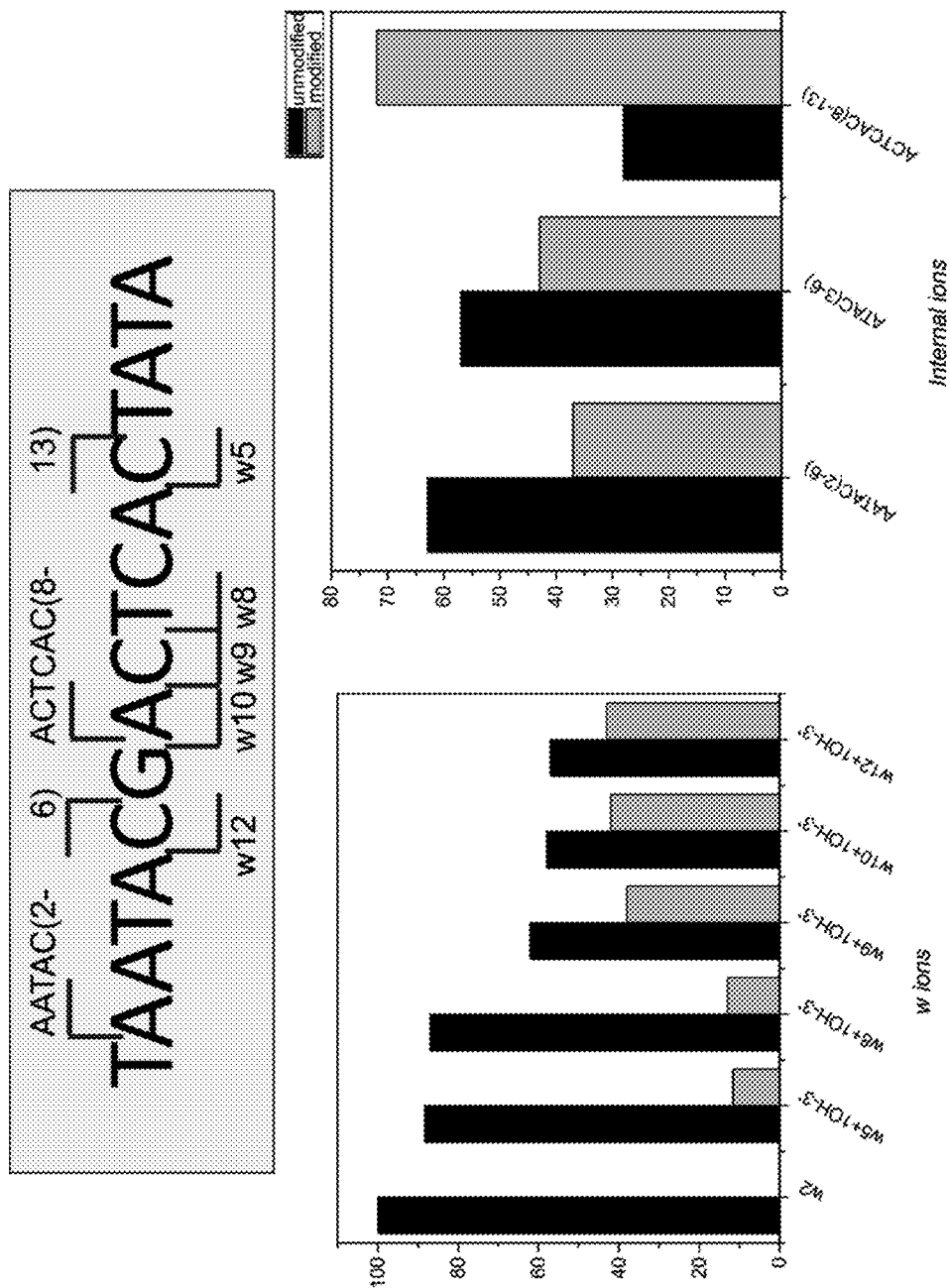
FIG. 7: MS/MS fragmentation patterns of monofluoroalkylated ss-DNA proving fluoroalkylation on cytosine nucleobase.

The MS-spectrum showed an approximately 10% conversion to the mono-fluoroalkylated derivative. The subsequent MS/MS fragmentation revealed that all fluoroalkylations can be traced to cytosine modification (FIG. 7).

INDUSTRIAL APPLICABILITY

The disclosed method can be used for C—H functionalization of aromatic substrates, covalent modification of peptides and proteins containing aromatic amino acids and nucleotides containing cytosine with fluoroalkyl groups (bioconjugation), analytical biochemistry, protein surface mapping and fluoroalkylation, epitope mapping via surface modification and protein crosslinking. Proteins containing solvent exposed tryptophane residues and oligonucleotides with cytosine nucleobases represent the most suitable substrates.

The invention claimed is:

1. A method for functionalization of an aromatic amino acid or a nucleobase with a fluoroalkyl-containing moiety $R_F$, wherein the aromatic amino acid or the nucleobase is reacted in the presence of at least one reductant with at least one hypervalent iodine fluoroalkyl reagent, wherein the hypervalent iodine fluoroalkyl reagent is of general formula 1

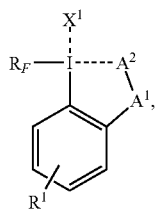

(1)

wherein $R^1$ is selected from H, C1-C4 alkyl, Me $(OCH_2CH_2)_nO$, wherein n=1-10, $X^1$ is not present or is selected from chloride, tetrafluoroborate, hexafluorophosphate, trifluoromethanesulfonate, methanesulfonate, toluenesulfonate, fluoride, bromide, $(F(CF_2)_sSO_2)_2N^-$, wherein s=1 to 4, C1-C6 carboxylate, fluorinated C1-C6 carboxylate, hexafluoroantimonate;

$A^1$ is not present or is selected from
carbonyl group (C=O),
$R^2$—C—$R^3$, wherein $R^2$ and $R^3$ are independently selected from fluorine, chlorine, hydrogen, $CF_3$, $C_1$-$C_4$ alkyl, phenyl, phenyl substituted by fluorine, chlorine and/or $C_1$-$C_4$ alkyl, omega-methoxy-($C_1$-$C_4$)alkyl; or $R^2$ and $R^3$ together with the carbon atom to which they are bound form 1,1-cyclobutylene, 1,1-cyclopentylene, 1,1-cyclohexylene, 1,1-(4-oxa-cyclohexylene);

$A^2$ is not present or is selected from
hydroxyl group (OH), -oxygen (—O—),
$C_{1-4}$ alkoxy, $OSiR^4R^5R^6$, wherein $R^4,R^5,R^6$ are independently selected from methyl, ethyl, n-propyl, i-propyl and phenyl;

$R^7N$, wherein $R^7$ is selected from $C_{1-10}$ alkyl, phenyl-substituted $C_{1-10}$ alkyl, and 4-chlorophenyl-substituted $C_{1-10}$ alkyl;

$R^8CO$—, wherein $R^8$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_mCOOQ$, wherein m=2-3, —$(CX_2)_m$ $SO_3Q$, wherein m=2-3, -phenyl-$SO_3Q$, -phenyl-COOQ, —$(CX_2)_mCOO$—, wherein m=2-3, —$(CX_2)_m$ $SO_3$—, wherein m=2-3, -phenyl-$SO_3$—, -phenyl-COO—, $X_2$=F or Cl, Q is selected from lithium, sodium, potassium, rubidium, cesium, tetra (C1-C4 alkyl, phenyl, benzyl) ammonium, tri (C1-C4 alkyl, phenyl, benzyl) pyridinium;

$R^9C(O)O$—, wherein $R^9$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_mCOOQ$, wherein m=2-3, —$(CX_2)_m$ $SO_3Q$, wherein m=2-3, -phenyl-$SO_3Q$, -phenyl-COOQ, —$(CX_2)_mCOO$—, wherein m=2-3, —$(CX_2)_m$ $SO_3$—, wherein m=2-3, -phenyl-$SO_3$—, -phenyl-COO—, $X_2$=F or Cl, Q is selected from lithium, sodium, potassium, rubidium, cesium, tetra (C1-C4 alkyl, phenyl, benzyl) ammonium, tri (C1-C4 alkyl, phenyl, benzyl) pyridinium;

$R_F$ is —$CF_2$-$A^3$-$A^4$, wherein $A^3$ is not present and $A^4$ is fluorine, or phenylsulfanyl (PhS) group, or $A^3$ is $CF_2$ and $A^4$ is fluorine, $C_{1-10}$ perfluoroalkyl, phenoxy, $C_{1-10}$ alkoxy, phenylsulfanyl, N-imidazolyl, N-pyrazolyl, N-benzimidazolyl, N-triazoyl, N-(2-methyl) imidazolyl, $CH_3$ $(OCH_2CH_2)_nO$, where n=1-10, $Cl^-MeH_2N^+(CH_2)_r$, wherein r=1-10, $Cl^-MeH_2N^+(CH_2)_2$-phenyloxy, $C_{1-10}$ alkyl, ethenyl, ethynyl, omega-azido $C_{1-10}$ alkyl, omega-amino $C_{1-10}$ alkyl, omega-ethynyl $C_{1-10}$ alkyl, $C_{1-10}$ alkylthio, phenyl, chloro, bromo, iodo, azido, nitro, $C_{1-10}$ alkoxycarbonyl-substituted phenyl, $C_{2-10}$ alkenyl, $C_{2-10}$ alkyl omega substituted with $SO_2F$, N-succinimide-O—C(O)—, methyldiaziridine, trifluoromethyldiaziridine, rhodamine, fluorescein or coumarin; aryl p-substituted with N-succinimide-O—C(O)—, rhodamine, fluorescein or coumarin, phenoxy p-substituted with N-succinimide-O—C(O)—, rhodamine, fluorescein or coumarin, and 2-(aryliodanyl)-1,1,2,2-tetrafluoroethyl; in alkyl chains, two neighboring carbon atoms may be replaced by a methylamido group (—N(Me)-C(O)—) and/or by a phenyl group.

2. The method of claim 1, wherein the aromatic amino acid is selected from phenylalanine, tryptophan, tyrosine, histidine.

3. The method of claim 1, wherein the aromatic amino acid is tryptophan.

4. The method of claim 1, wherein the nucleobase is cytosine.

5. The method of claim 1, wherein the reductant is selected from a group consisting of sodium ascorbate, potassium ascorbate, calcium ascorbate, magnesium ascorbate, esters of ascorbic acid with carboxylic acids of the formula $R^{10}CO_2H$ wherein $R^{10}$ is $C_{1-18}$ alkyl, sodium sulphite, sodium dithionite, tetrakis(dimethylamino)ethylene, sodium phosphite, sodium hypophosphite, and sodium hydroxymethanesulfinate.

6. The method of claim 1, wherein the reductant is used in an amount of 0.5-1.0 equivalents, relative to the hypervalent iodine fluoroalkyl reagent.

7. The method of claim 1, wherein aromatic amino acids incorporated in a protein are reacted in the presence of at least one reductant with at least one hypervalent iodine fluoroalkyl reagent, and subsequently it is detected which amino acids are fluoroalkylated and these amino acids are then determined to be present on the solvent-exposed surface of the protein.

8. The method of claim 1, wherein the reductant is used in an amount of 0.9-1.1 equivalents, relative to the hypervalent iodine fluoroalkyl reagent.

9. A method for functionalization of an aromatic amino acid or a nucleobase with a fluoroalkyl-containing moiety $R_F$, wherein the aromatic amino acid or the nucleobase is reacted in the presence of at least one reductant with at least one hypervalent iodine fluoroalkyl reagent, wherein the hypervalent iodine fluoroalkyl reagent is of general formula 1

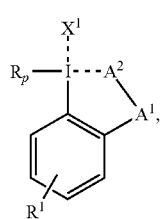

(1)

wherein $R^1$ is selected from H, C1-C4 alkyl, $Me(OCH_2CH_2)_nO$, wherein n=1-10, $X^1$ is not present or is selected from chloride, tetrafluoroborate, hexafluorophosphate, trifluoromethanesulfonate, methanesulfonate, toluenesulfonate, fluoride, bromide, $(F(CF_2)_sSO_2)_2N$, wherein s=1 to 4, C1-C6 carboxylate, fluorinated C1-C6 carboxylate, hexafluoroantimonate;

$A^1$ is not present or is selected from
carbonyl group (C=O),
$R^2$—C—$R^3$, wherein $R^2$ and $R^3$ are independently selected from fluorine, chlorine, hydrogen, $CF_3$, $C_1$-$C_4$ alkyl, phenyl, phenyl substituted by fluorine, chlorine and/or $C_1$-$C_4$ alkyl, omega-methoxy-($C_1$-$C_4$)alkyl; or $R^2$ and $R^3$ together with the carbon atom to which they are bound form 1,1-cyclobutylene, 1,1-cyclopentylene, 1,1-cyclohexylene, 1,1-(4-oxacyclohexylene);

$A^2$ is not present or is selected from
hydroxyl group (OH),
oxygen (—O—),
$C_{1-4}$ alkoxy,
$OSiR^4R^5R^6$, wherein $R^4,R^5,R^6$ are independently selected from methyl, ethyl, n-propyl, i-propyl and phenyl;
$R^7N$, wherein $R^7$ is selected from $C_{1-10}$ alkyl, phenyl-substituted $C_{1-10}$ alkyl, and 4-chlorophenyl-substituted $C_{1-10}$ alkyl;
$R^8CO$—, wherein $R^8$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_mCOOQ$, wherein m=2-3, —$(CX_2)_mSO_3Q$, wherein m=2-3, -phenyl-$SO_3Q$, -phenyl-COOQ, —$(CX_2)_mCOO$—, wherein m=2-3, —$(CX_2)_m$ $SO_3$—, wherein m=2-3, -phenyl-$SO_3$—, -phenyl-COO—,
$X^2$=F or Cl,
Q is selected from lithium, sodium, potassium, rubidium, cesium, tetra ($C_1$-$C_4$ alkyl, phenyl, benzyl) ammonium, tri ($C_1$-$C_4$ alkyl, phenyl, benzyl) pyridinium;
$R^9C(O)O$—, wherein $R^9$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_mCOOQ$, wherein m=2-3, —$(CX_2)_mSO_3Q$, wherein m=2-3, -phenyl-$SO_3Q$, -phenyl-COOQ, —$(CX_2)_mCOO$—, wherein m=2-3, —$(CX_2)_m$ $SO_3$—, wherein m=2-3, -phenyl-$SO_3$—, -phenyl-COO—,
$X^2$=F or Cl,
Q is selected from lithium, sodium, potassium, rubidium, cesium, tetra (C1-C4 alkyl, phenyl, benzyl) ammonium, tri (C1-C4 alkyl, phenyl, benzyl) pyridinium;

$R_F$ is-$CF_2$-$A^3$-$A^4$, wherein
$A^3$ is not present and $A^4$ is fluorine, or phenylsulfanyl (PhS) group, or
$A^3$ is $CF_2$ and $A^4$ is fluorine, $C_{1-10}$ perfluoroalkyl, phenoxy, C1-10 alkoxy, phenylsulfanyl, N-imidazolyl, N-pyrazolyl, N-benzimidazolyl, N-triazoyl, N-(2-methyl) imidazolyl, $CH_3$ $(OCH_2CH_2)_nO$, where n=1-10, $Cl^-MeH_2N^+(CH_2)_r$, wherein r=1-10, $Cl^-MeH_2N^+(CH_2)_2$-phenyloxy, $C_{1-10}$ alkyl, ethenyl, ethynyl, omega-azido $C_{1-10}$ alkyl, omega-amino $C_{1-10}$ alkyl, omega-ethynyl $C_{1-10}$ alkyl, $C_{1-10}$ alkylthio, phenyl, chloro, bromo, iodo, azido, nitro, $C_{1-10}$ alkoxycarbonyl-substituted phenyl, $C_{2-10}$ alkenyl, $C_{2-10}$ alkyl omega substituted with $SO_2F$, N-succinimide-O—C(O)—, methyldiaziridine, trifluoromethyldiaziridine, rhodamine, fluorescein or coumarin; aryl p-substituted with N-succinimide-O—C(O)—, rhodamine, fluorescein or coumarin, phenoxy p-substituted with N-succinimide-O—C(O)—, rhodamine, fluorescein or coumarin, and 2-(aryliodanyl)-1,1,2,2-tetrafluoroethyl; in alkyl chains, two neighboring carbon atoms may be replaced by a methylamido group (—N(Me)-C(O)—) and/or by a phenyl group;

wherein the hypervalent iodine fluoroalkyl reagent is selected from the group consisting of the following reagents:

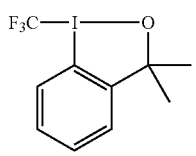
1a

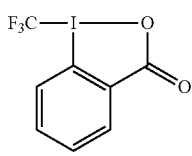
1b

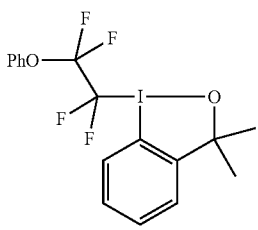
1c

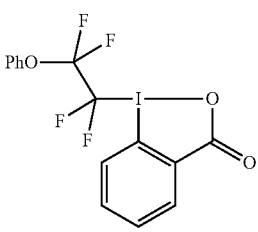
1d

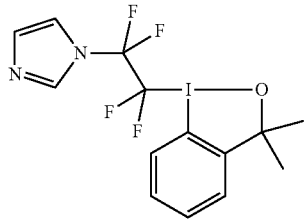
1e

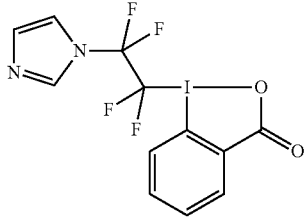
1f

-continued

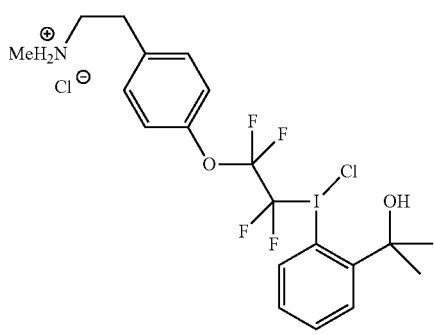
1g

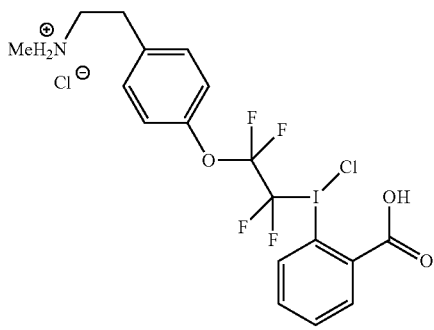
1h

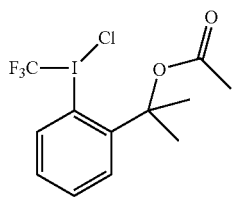
1i

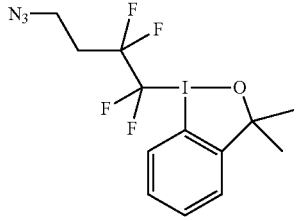
1j

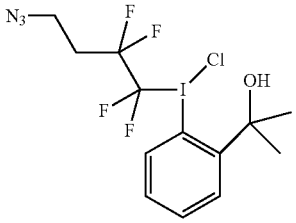
1k

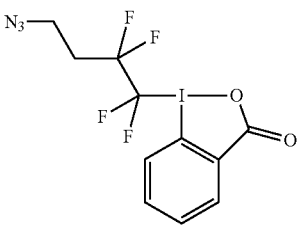
1l

-continued

1m 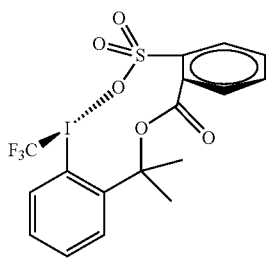

1n 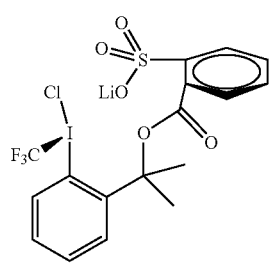

1o 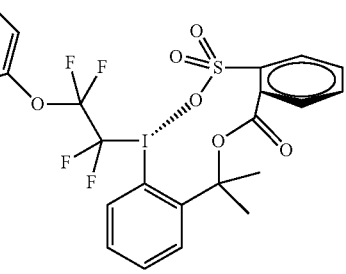

1p 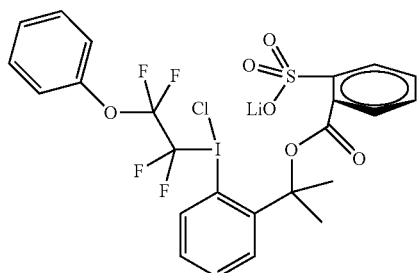

1q 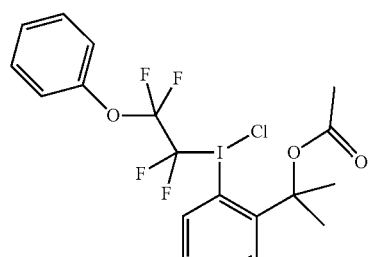

-continued

1r 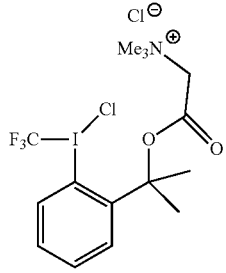

1s 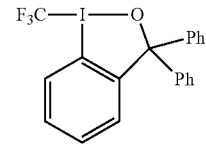

1t 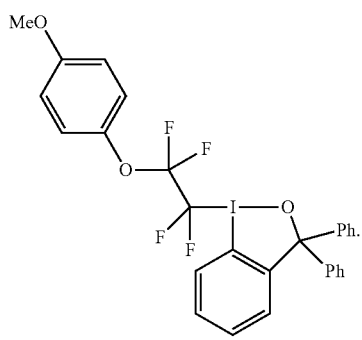

10. A hypervalent iodine fluoroalkyl reagent of general formula 1-1

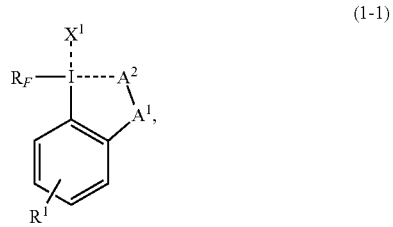
(1-1)

wherein $R^1$ is selected from H, C1-C4 alkyl, Me(OCH$_2$CH$_2$)$_n$O, wherein n=1-10, $X^1$ is not present or is selected from chloride, tetrafluoroborate, hexafluorophosphate, trifluoromethanesulfonate, methanesulfonate, toluenesulfonate, fluoride, bromide, (F(CF$_2$)$_s$SO$_2$)$_2$N$^-$, wherein s=1 to 4, C1-C6 carboxylate, fluorinated C1-C6 carboxylate, hexafluoroantimonate;

$A^1$ is selected from $R^2$—C—$R^3$, where $R^2$ and $R^3$ are independently selected from chlorine, CF$_3$, phenyl, phenyl substituted by fluorine, chlorine and/or C$_1$-C$_4$ alkyl, omega-methoxy-(C$_1$-C$_4$)alkyl;

or $R^2$ and $R^3$ together with the carbon atom to which they are bound form 1,1-cyclobutylene, 1,1-cyclopentylene, 1,1-cyclohexylene, 1,1-(4-oxacyclohexylene);

A² is selected from
hydroxyl group (OH),
oxygen (—O—),
$C_{1-4}$ alkoxy,
$OSiR^4R^5R^6$, wherein $R^4,R^5,R^6$ are independently selected from methyl, ethyl, n-propyl, i-propyl and phenyl;
$R^7N$, wherein $R^7$ is selected from $C_{1-10}$ alkyl, phenyl-substituted $C_{1-10}$ alkyl, and 4-chlorophenyl-substituted $C_{1-10}$ alkyl;
$R^8CO$—, wherein $R^8$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_m COOQ$, wherein m=2-3, —$(CX_2)_m SO_3Q$, wherein m=2-3, -phenyl-$SO_3Q$, -phenyl-COOQ, —$(CX_2)_m COO$—, wherein m=2-3, —$(CX_2)_m SO_3$—, wherein m=2-3, -phenyl-$SO_3$—, -phenyl-COO—,
$X_2$=F or Cl,
Q is selected from lithium, sodium, potassium, rubidium, cesium, tetra (C1-C4 alkyl, phenyl, benzyl) ammonium, tri (C1-C4 alkyl, phenyl, benzyl) pyridinium;
$R^9C(O)O$—, wherein $R^9$ is selected from $C_{1-10}$ alkyl, phenyl-substituted $C_{1-10}$ alkyl, $CH_3(OCH_2CH_2)_o$—, wherein o=1-10, $Cl^-Me_3N^+(CH_2)_p$—, wherein p=1-10, —$(CX_2)_m COOQ$, wherein m=2-3, —$(CX_2)_m SO_3Q$, wherein m=2-3, -phenyl-$SO_3Q$, -phenyl-COOQ, —$(CX_2)_m COO$—, wherein m=2-3, —$(CX_2)_m SO_3$—, wherein m=2-3, -phenyl-$SO_3$—, -phenyl-COO—,
$X_2$=F or Cl,
Q is selected from lithium, sodium, potassium, rubidium, cesium, tetra (C1-C4 alkyl, phenyl, benzyl) ammonium, tri (C1-C4 alkyl, phenyl, benzyl) pyridinium;
$R_F$ is —$CF_2$-$A^3$-$A^4$, wherein
$A^3$ is not present and $A^4$ is fluorine, or phenylsulfanyl (PhS) group, or
$A^3$ is $CF_2$ and $A^4$ is fluorine, $C_{1-10}$ perfluoroalkyl, phenoxy, C1-10 alkoxy, phenylsulfanyl, N-imidazolyl, N-pyrazolyl, N-benzimidazolyl, N-triazoyl, N-(2-methyl) imidazolyl, $CH_3(OCH_2CH_2)_nO$, where n=1-10, $Cl^-MeH_2N^+(CH_2)_r$, wherein r=1-10, $Cl^-MeH_2N^+(CH_2)_2$-phenyloxy, $C_{1-10}$ alkyl, ethenyl, ethynyl, omega-azido $C_{1-10}$ alkyl, omega-amino $C_{1-10}$ alkyl, omega-ethynyl $C_{1-10}$ alkyl, $C_{1-10}$ alkylthio, phenyl, chloro, bromo, iodo, azido, nitro, $C_{1-10}$ alkoxycarbonyl-substituted phenyl, $C_{2-10}$ alkenyl, $C_{2-10}$ alkyl omega substituted with $SO_2F$, N-succinimide-O—C(O)—, methyldiaziridine, trifluoromethyldiaziridine, rhodamine, fluorescein or coumarin; aryl p-substituted with N-succinimide-O—C(O)—, rhodamine, fluorescein or coumarin, phenoxy p-substituted with N-succinimide-O—C(O)—, rhodamine, fluorescein or coumarin, and 2-(aryliodanyl)-1,1,2,2-tetrafluoroethyl; in alkyl chains, two neighboring carbon atoms may be replaced by a methylamido group (—N(Me)-C(O)—) and/or by a phenyl group,
provided that:
A2 is not —O— or —OH, when: $X^1$ is not present, $R_F$ is $CF_3$ and A1 is $R^2$—C—$R^3$, wherein $R^2$ and $R^3$ are $CF_3$ or wherein $R^2$ and $R^3$ together form 1,1-cyclohexylene.

11. A hypervalent iodine fluoroalkyl reagent selected from the following compounds:

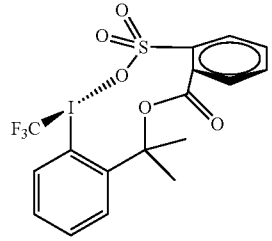

1m

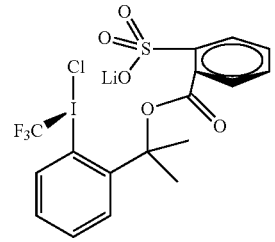

1n

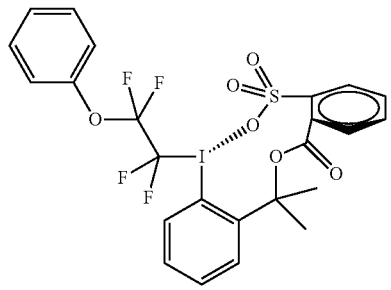

1o

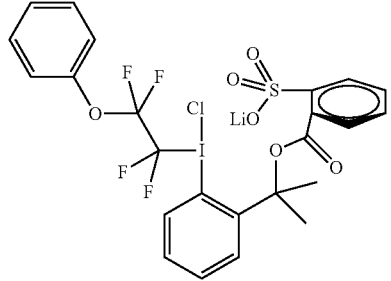

1p

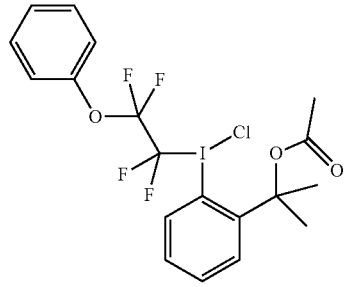

1q

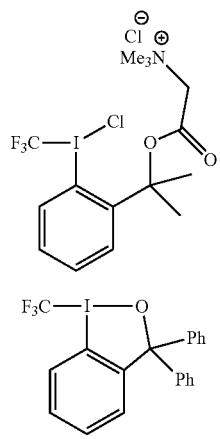
1r
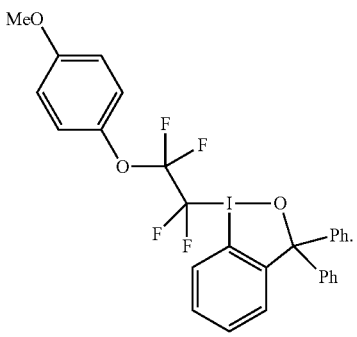
1t
1s
* * * * *

```
                         SEQUENCE LISTING

<160> NUMBER OF SEQ ID NOS: 7

<210> SEQ ID NO 1
<211> LENGTH: 11
<212> TYPE: PRT
<213> ORGANISM: artificial
<220> FEATURE:
<223> OTHER INFORMATION: peptide fluoroalkylated in Example IV

<400> SEQUENCE: 1

Ala Phe Arg Ile Pro Leu Tyr Trp Gly Arg Ile
1               5                   10

<210> SEQ ID NO 2
<211> LENGTH: 17
<212> TYPE: DNA
<213> ORGANISM: artificial
<220> FEATURE:
<223> OTHER INFORMATION: ss-DNA labeled by fluoroalkylation in Example
      XII

<400> SEQUENCE: 2
taatacgact cactata                                                    17

<210> SEQ ID NO 3
<211> LENGTH: 10
<212> TYPE: PRT
<213> ORGANISM: artificial
<220> FEATURE:
<223> OTHER INFORMATION: sequence fluoroalkylated in Fig. 5A

<400> SEQUENCE: 3

Ala Ser Pro Asp Trp Gly Tyr Asp Asp Lys
1               5                   10

<210> SEQ ID NO 4
<211> LENGTH: 9
<212> TYPE: PRT
<213> ORGANISM: artificial
<220> FEATURE:
<223> OTHER INFORMATION: sequence fluoroalkylated in Fig. 5B

<400> SEQUENCE: 4

Gly Gly Pro Phe Ser Asp Ser Tyr Arg
1               5

<210> SEQ ID NO 5
<211> LENGTH: 14
<212> TYPE: PRT
<213> ORGANISM: artificial
<220> FEATURE:
<223> OTHER INFORMATION: sequence fluoroalkylated in Fig. 5C

<400> SEQUENCE: 5

Glu Ser Ile Ser Val Ser Ser Glu Gln Leu Ala Gln Phe Arg
1               5                   10
```

```
<210> SEQ ID NO 6
<211> LENGTH: 19
<212> TYPE: PRT
<213> ORGANISM: artificial
<220> FEATURE:
<223> OTHER INFORMATION: sequence fluoroalkylated in Fig. 5D

<400> SEQUENCE: 6

Glu Ile Ile Asn Val Gly His Ser Phe His Val Asn Phe Glu Asp Asn
1               5                   10                  15

Asp Asn Arg

<210> SEQ ID NO 7
<211> LENGTH: 17
<212> TYPE: DNA
<213> ORGANISM: artificial
<220> FEATURE:
<223> OTHER INFORMATION: nucleotide sequence shown in Fig. 7

<400> SEQUENCE: 7
taatacgact cactata                                              17
```